US007988697B2

(12) United States Patent
Miller et al.

(10) Patent No.: US 7,988,697 B2
(45) Date of Patent: Aug. 2, 2011

(54) GRAFT FIXATION DEVICE AND METHOD

(75) Inventors: M. Todd Miller, Saratoga, CA (US);
Ryan E. Yearsley, Palo Alto, CA (US);
Lonnie E. Paulos, Salt Lake City, UT (US)

(73) Assignee: Stryker Endoscopy, San Jose, CA (US)

( * ) Notice: Subject to any disclaimer, the term of this patent is extended or adjusted under 35 U.S.C. 154(b) by 70 days.

(21) Appl. No.: 11/466,689

(22) Filed: Aug. 23, 2006

(65) Prior Publication Data

US 2006/0293689 A1 Dec. 28, 2006

Related U.S. Application Data

(62) Division of application No. 10/283,010, filed on Oct. 29, 2002, now Pat. No. 7,588,595.

(51) Int. Cl.
*A61B 17/58* (2006.01)
*A61B 17/60* (2006.01)
*A61F 2/00* (2006.01)

(52) U.S. Cl. ........................................................ 606/98
(58) Field of Classification Search .................. 606/59, 606/64, 73, 75, 95–96, 300–301, 304, 309, 606/321, 232, 323, 98, 103; 623/13.14
See application file for complete search history.

(56) References Cited

U.S. PATENT DOCUMENTS

| 2,523,239 A | | 9/1950 | Tinnerman | |
|---|---|---|---|---|
| 2,927,497 A | * | 3/1960 | Rapata | 411/508 |
| 3,499,222 A | * | 3/1970 | Edelman et al. | 433/174 |
| 3,810,279 A | | 5/1974 | Swick et al. | |
| 4,077,300 A | * | 3/1978 | Yoda | 411/15 |
| 4,116,106 A | | 9/1978 | Barbour | |
| D269,759 S | | 7/1983 | Wollar | |
| 4,772,286 A | | 9/1988 | Goble et al. | |
| 4,901,711 A | | 2/1990 | Goble et al. | |
| 4,976,715 A | | 12/1990 | Bays et al. | |
| 4,985,032 A | | 1/1991 | Goble et al. | |
| 5,062,843 A | * | 11/1991 | Mahony, III | 606/73 |
| 5,122,133 A | * | 6/1992 | Evans | 606/73 |
| 5,129,906 A | * | 7/1992 | Ross et al. | 606/77 |
| 5,203,784 A | * | 4/1993 | Ross et al. | 606/104 |
| RE34,293 E | | 6/1993 | Goble et al. | |
| 5,234,434 A | | 8/1993 | Goble et al. | |
| 5,246,441 A | | 9/1993 | Ross et al. | |
| 5,261,914 A | | 11/1993 | Warren | |

(Continued)

OTHER PUBLICATIONS

Office Action from related U.S. Appl. No. 10/283,010 dated Sep. 21 2005 (8 pages).

(Continued)

*Primary Examiner* — Thomas C Barrett
*Assistant Examiner* — Sameh Boles
(74) *Attorney, Agent, or Firm* — Workman Nydegger

(57) ABSTRACT

A system for securing a graft within a bone includes a tubular cross pin having an interior surface bounding a passageway extending between a proximal end and an opposing distal end, the distal end terminating at a distal end face. A guide pin has an exterior surface extending between a proximal end and an opposing distal end, the exterior surface including an outwardly projecting shoulder. The guide pin is removably received within the passageway of the cross pin such that the distal end face of the cross pin biases against the shoulder and a proximal portion of the guide pin freely projects beyond the proximal end of the cross pin.

23 Claims, 24 Drawing Sheets

U.S. PATENT DOCUMENTS

| | | | |
|---|---|---|---|
| 5,314,429 A | | 5/1994 | Goble |
| 5,350,380 A | | 9/1994 | Goble et al. |
| 5,374,270 A | * | 12/1994 | McGuire et al. ............... 606/80 |
| 5,380,334 A | * | 1/1995 | Torrie et al. ................. 606/104 |
| 5,385,567 A | | 1/1995 | Goble |
| 5,393,302 A | | 2/1995 | Clark et al. |
| 5,397,356 A | | 3/1995 | Goble |
| 5,431,651 A | | 7/1995 | Goble |
| 5,466,243 A | | 11/1995 | Schmieding et al. |
| 5,480,166 A | * | 1/1996 | Milsop ......................... 279/143 |
| 5,484,437 A | * | 1/1996 | Michelson ................. 606/86 A |
| 5,545,180 A | * | 8/1996 | Le et al. ........................ 606/232 |
| 5,562,671 A | | 10/1996 | Goble et al. |
| 5,601,558 A | * | 2/1997 | Torrie et al. .................... 606/72 |
| 5,601,562 A | | 2/1997 | Wolf et al. |
| 5,779,703 A | | 7/1998 | Bonoist |
| 5,849,013 A | | 12/1998 | Whittaker et al. |
| 5,891,150 A | | 4/1999 | Chan |
| 5,895,425 A | | 4/1999 | Grafton et al. |
| 5,918,604 A | | 7/1999 | Whelan |
| 6,066,173 A | | 5/2000 | McKernan et al. |
| 6,096,060 A | * | 8/2000 | Fitts et al. ..................... 606/232 |
| 6,113,604 A | | 9/2000 | Whittaker et al. |
| 6,132,433 A | | 10/2000 | Whelan |
| 6,139,565 A | | 10/2000 | Stone et al. |
| 6,146,387 A | | 11/2000 | Trott et al. |
| 6,203,572 B1 | | 3/2001 | Johnson et al. |
| 6,306,138 B1 | | 10/2001 | Clark et al. |
| 6,544,281 B2 | * | 4/2003 | ElAttrache et al. ........... 606/232 |
| 6,554,852 B1 | * | 4/2003 | Oberlander ................... 606/232 |
| 6,592,587 B1 | * | 7/2003 | Roger ........................... 606/318 |
| 6,623,492 B1 | | 9/2003 | Berube et al. |
| 6,743,232 B2 | * | 6/2004 | Overaker et al. ............... 606/72 |

OTHER PUBLICATIONS

Office Action from related U.S. Appl. No. 10/283,010 dated Feb. 23, 2006 (6 pages).
Office Action from related U.S. Appl. No. 10/283,010 dated Sep. 27, 2006 (6 pages).
Office Action from related U.S. Appl. No. 10/283,010 dated Mar. 12, 2007 (5 pages).
Office Action from related U.S. Appl. No. 10/283,010 dated Aug. 13, 2007 (5 pages).
Office Action from related U.S. Appl. No. 10/283,010 dated Feb. 4, 2008 (5 pages).
Office Action from related U.S. Appl. No. 10/283,010 dated Dec. 4, 2008 (6 pages).
Notice of Allowance from related U.S. Appl. No. 10/283,010 dated Jun. 1, 2009 (6 pages).

* cited by examiner

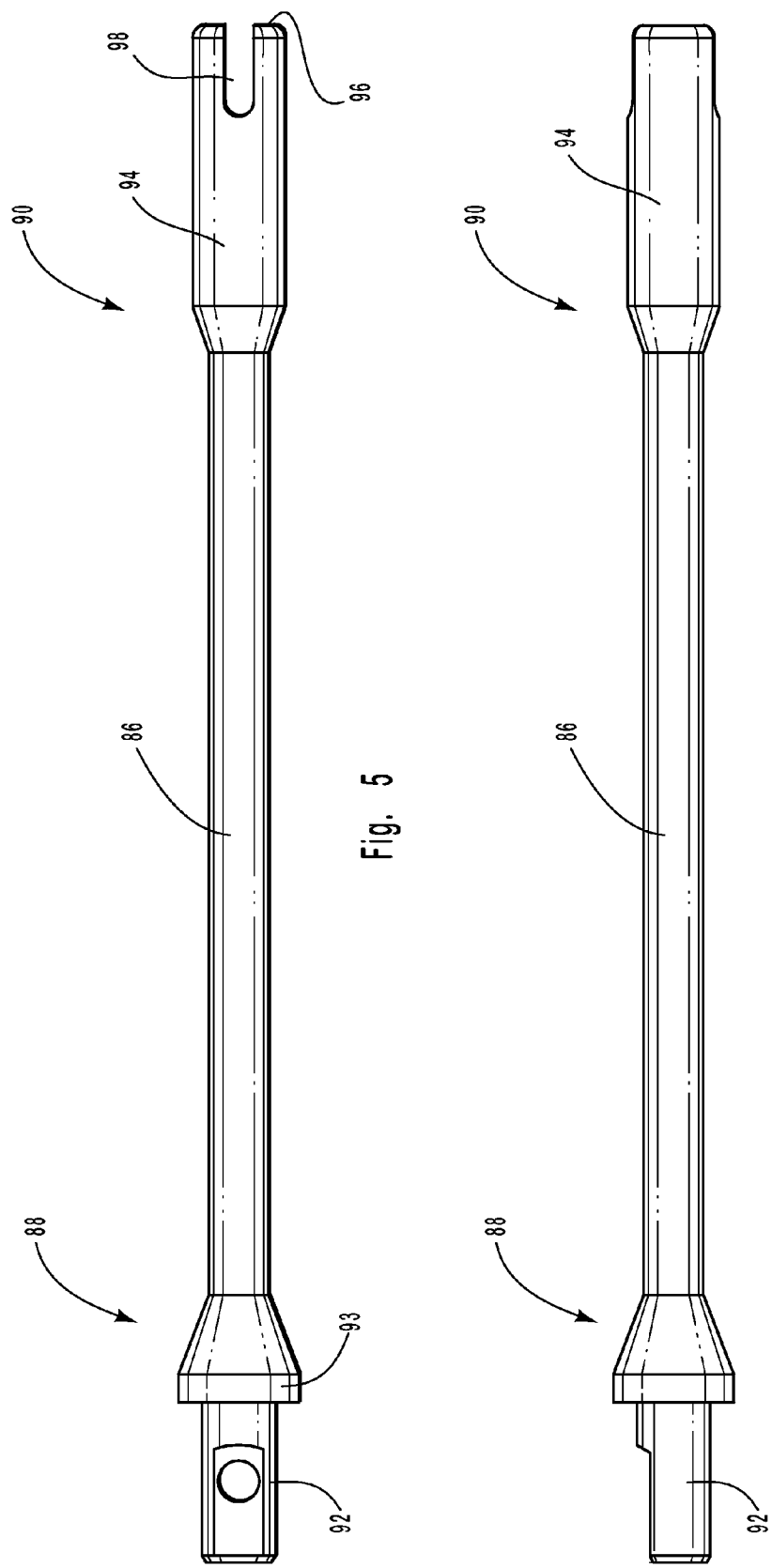

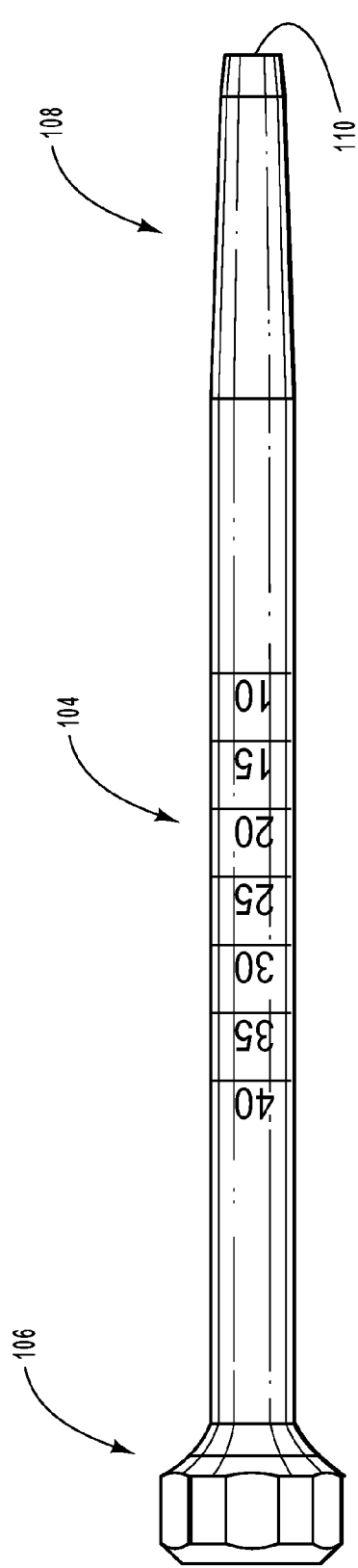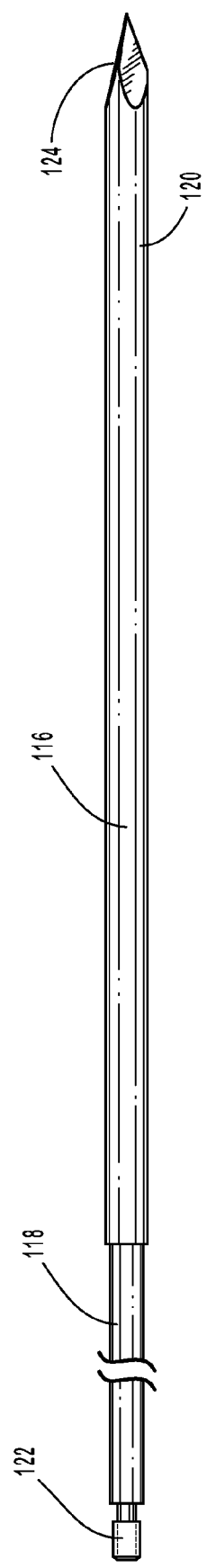
Fig. 8
Fig. 9

US 7,988,697 B2

GRAFT FIXATION DEVICE AND METHOD

CROSS-REFERENCE TO RELATED APPLICATIONS

This application is a divisional of patent application Ser. No. 10/283,010, filed Oct. 29, 2002, which is incorporated herein by reference.

BACKGROUND OF THE INVENTION

1. The Field of the Invention

The present invention relates to methods and devices for fixing graft to bone, and more specifically to fixing the anterior cruciate ligament (ACL) to the knee.

2. The Relevant Technology

Damaged or torn ligaments are commonly reconstructed using graft tissue either from a donor, referred to as an allograft, or from the patient, referred to as an autograft. Various methods are known in the arts for reattaching ligaments to bone, particularly for reconstruction of the ACL in the knee joint. Historically, graft fixation devices have been fashioned from metals, such as stainless steel and titanium alloys, but more recently, graft fixation devices are fabricated from biodegradable materials.

These newer materials do not have the same strength, toughness, or hardness as metals, and they present unsolved challenges for obtaining rigid and reliable fixation of the graft to the bone. For example, biodegradable and biological fixation devices are typically too brittle to permit impaction of a fixation pin into bone. Additionally, the low strength of these biodegradable and biological materials makes a fixation device very challenging to design such that it can be driven into bone under torque without a torsional failure occurring before the device is fully positioned to fixate a graft.

Furthermore, a biodegradable or biological fixation device can be especially difficult to remove once it is fully positioned within the bone. Because the graft reconstruction may not be perfect upon delivery of the fixation device, it is a significant disadvantage if a surgeon is unable to easily remove the fixation device in order to reposition the graft. Another problem with biodegradable or biological devices is it can be difficult to determine the position of the device within the host site under standard imaging methods.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 5 is a top plan view of a femoral index guide forming a portion of the drill guide shown in FIG. 4;

FIG. 6 is an elevated side view of the femoral index guide shown in FIG. 5;

FIG. 8 is an elevated side view of a guide bullet forming a portion of the drill guide shown in FIG. 4;

FIG. 9 is an elevated side view of the drill pin going laterally through the knee shown in FIG. 7;

DETAILED DESCRIPTION OF THE PREFERRED EMBODIMENTS

The present invention relates to methods and systems for fixing a graft, such as a ligament, to bone. By way of illustration, set forth below is an example of one embodiment of the inventive system used in fixing an anterior cruciate ligament in a knee joint. In alternative embodiments, it is appreciated that the inventive systems and methods or portions thereof can also be used where a cross pin is implement for securing other ligaments, such as the posterior cruciate ligament, or other soft tissue to bone.

Figure 1:
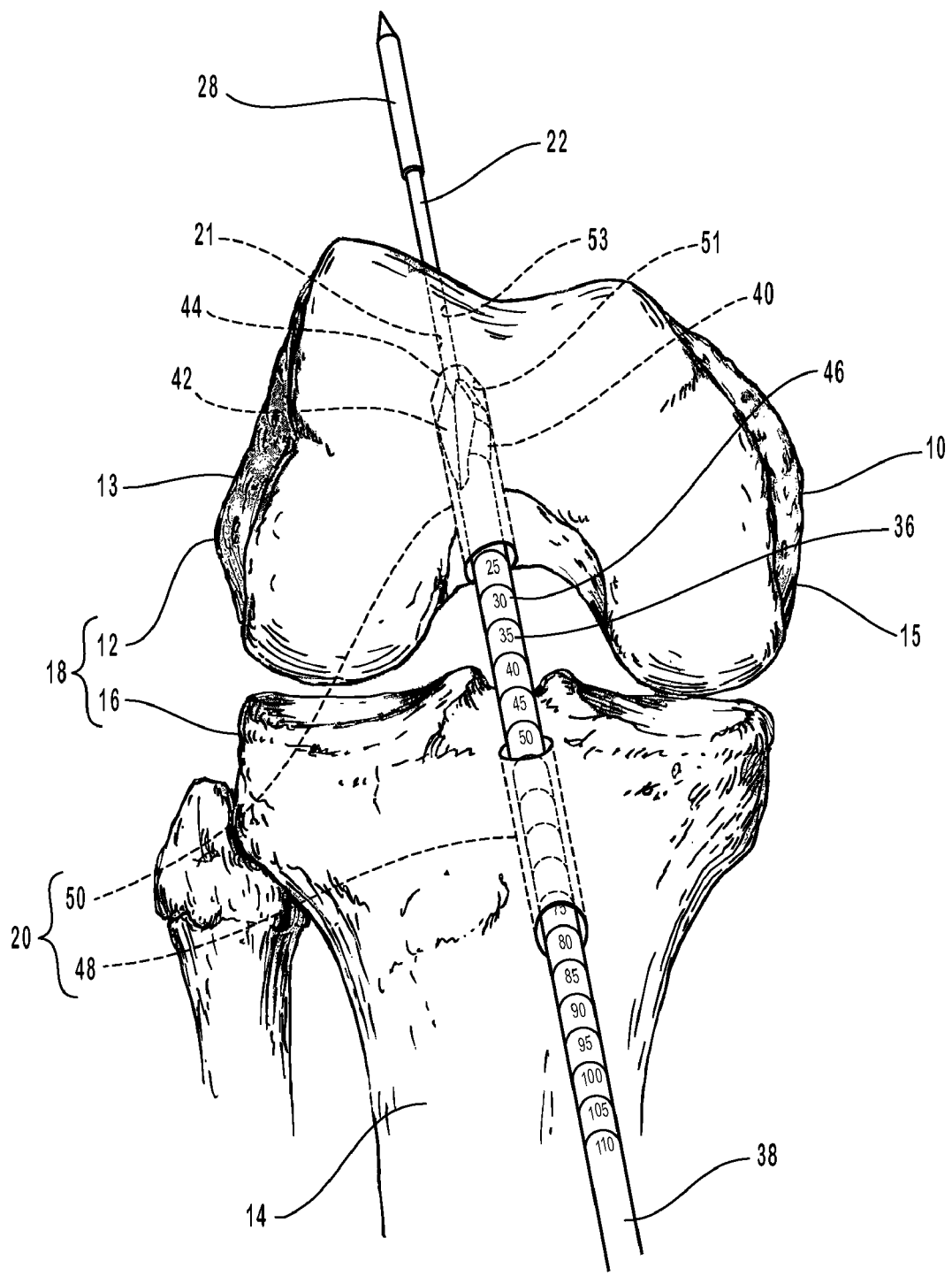
FIG. 1 is a front view of knee joint having a drill pin and a reamer forming a placement tunnel therein.

Depicted in FIG. 1 is a femur 10 which terminates distally at a femoral head 12. Femoral head 12 has a lateral side 13 and an opposing medial side 15. Also depicted is a tibia 14 which terminates proximally at a tibial plateau 16. Femoral head 12 articulates against tibial plateau 16 so as to form a knee joint 18.

Figure 2:
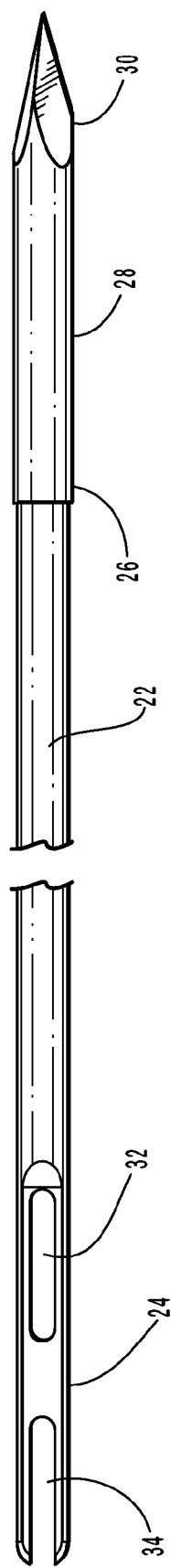
FIG. 2 is an elevated side view of the drill pin shown in FIG. 1.

To facilitate replacement of the anterior cruciate ligament, a placement tunnel 20 is formed in knee joint 18 at an angle that replicates the position of the natural anterior cruciate ligament. Placement tunnel 20 is formed in a two-step process. First, a drill pin 22 is passed from the anterior surface of tibia 14 upwardly through tibial plateau 16, and on upwardly through femoral head 12 of femur 10. Drill pin 22 forms a pilot tunnel 21 that extends completely through tibial plateau 16 and femoral head 12. As depicted in FIG. 2, drill pin 22 has a proximal end 24 and an opposing distal end 26. Located at distal end 26 is an enlarged head 28 that terminates at a sharpened drilling tip 30. For reasons as will be discussed below in great detail, proximal end 24 has an aperture 32 extending therethrough and terminates at a forked tip 34.

Drill pin 22 is inserted by removeably fixing a drill to proximal end 24. Drill pin 22 is then drilled through knee joint 18 as set forth above. Proper placement of drill pin 22 can be monitored by using an endoscope, x-rays, fluoroscope, or the like.

Once drill pin 22 is appropriately positioned, the drill is removed therefrom and a cannulated reamer 36 is slidably received over proximal end 24 of drill pin 22. As depicted in FIG. 1, reamer 36 has a proximal end 38 and an opposing distal end 40. Distal end 40 terminates an enlarged fluted drill head 42. A passageway 44 extends centrally along the length of reamer 36. Markings 46 are spaced longitudinally along the exterior surface of reamer 36 so as to enable placement of reamer 36 to a proper depth.

To facilitate placement, a drill is removable mounted on proximal end 38 of reamer 36. Using drill pin 22 as a guide, distal end 40 of reamer 36 is advanced over drill pin 22 so as to upwardly drill through tibial plateau 16, thereby forming tibial tunnel 48. Reamer 36 is then further advanced over drill pin 22 so as to drill a distance into femoral head 12, thereby forming femoral tunnel 50. Femoral tunnel 50 typically has a depth in a range between about 25 cm to about 30 cm but can be any desired depth depending on the situation. Tibial tunnel 48 and femoral tunnel 50 combine to form placement tunnel 20 which is sized to receive the replacement graft for the anterior cruciate ligament. An access tunnel 53 comprises the portion of pilot tunnel 21 extending between femoral tunnel 50 and the exterior of femoral head 12. It is noted that femoral tunnel 50 has an inner diameter larger than the inner diameter of access tunnel 53. As such, a shoulder 51 is formed extending between access tunnel 53 and the outer wall of femoral tunnel 50.

In alternative embodiments, it is appreciated that placement tunnel 20 can be formed using a variety of different apparatus and techniques which can comprise one or three or more different drilling steps.

Figure 3:
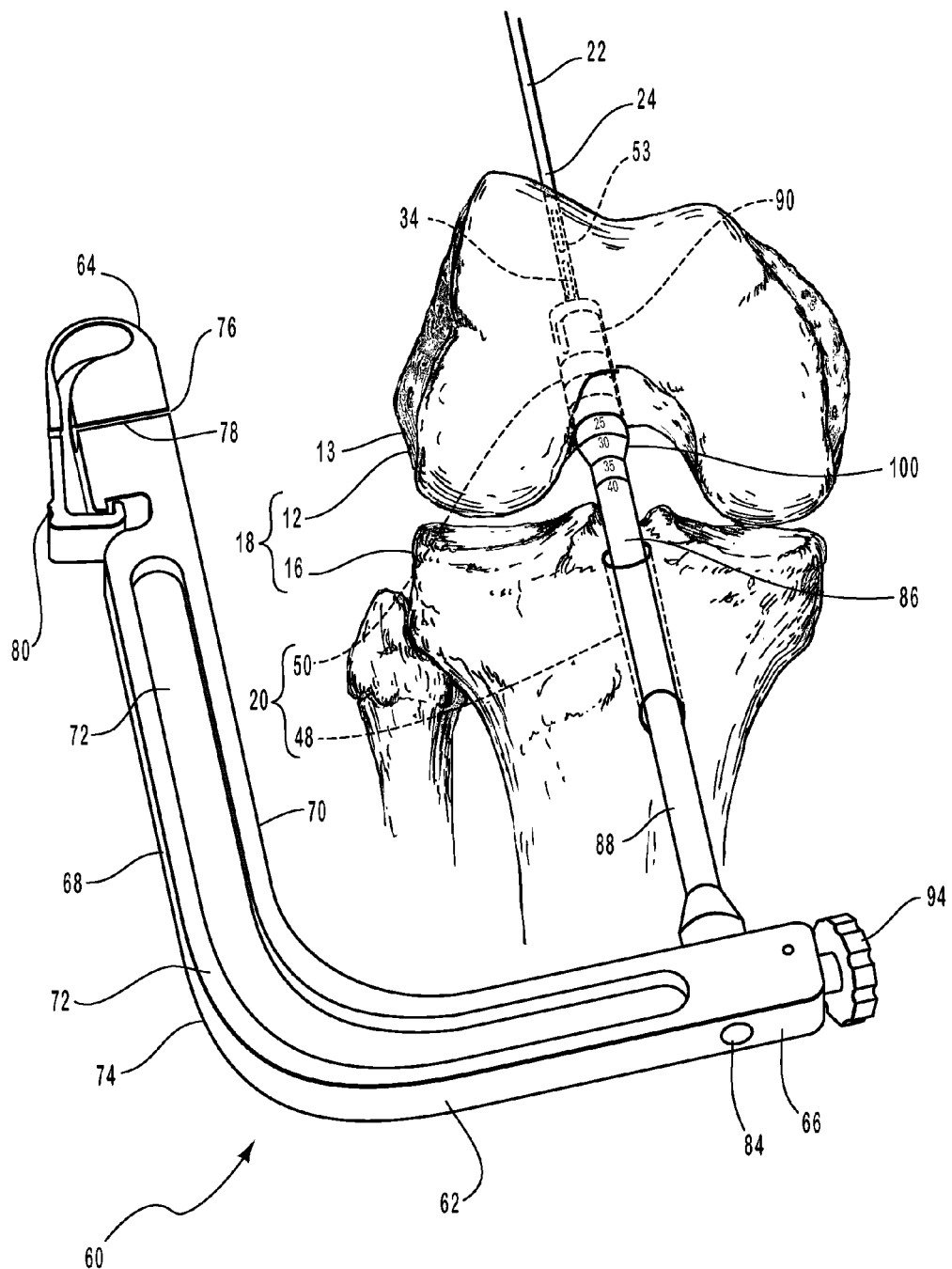
FIG. 3 is a front perspective view of a portion of a drill guide inserted in the knee shown in FIG. 1.
Figure 4:
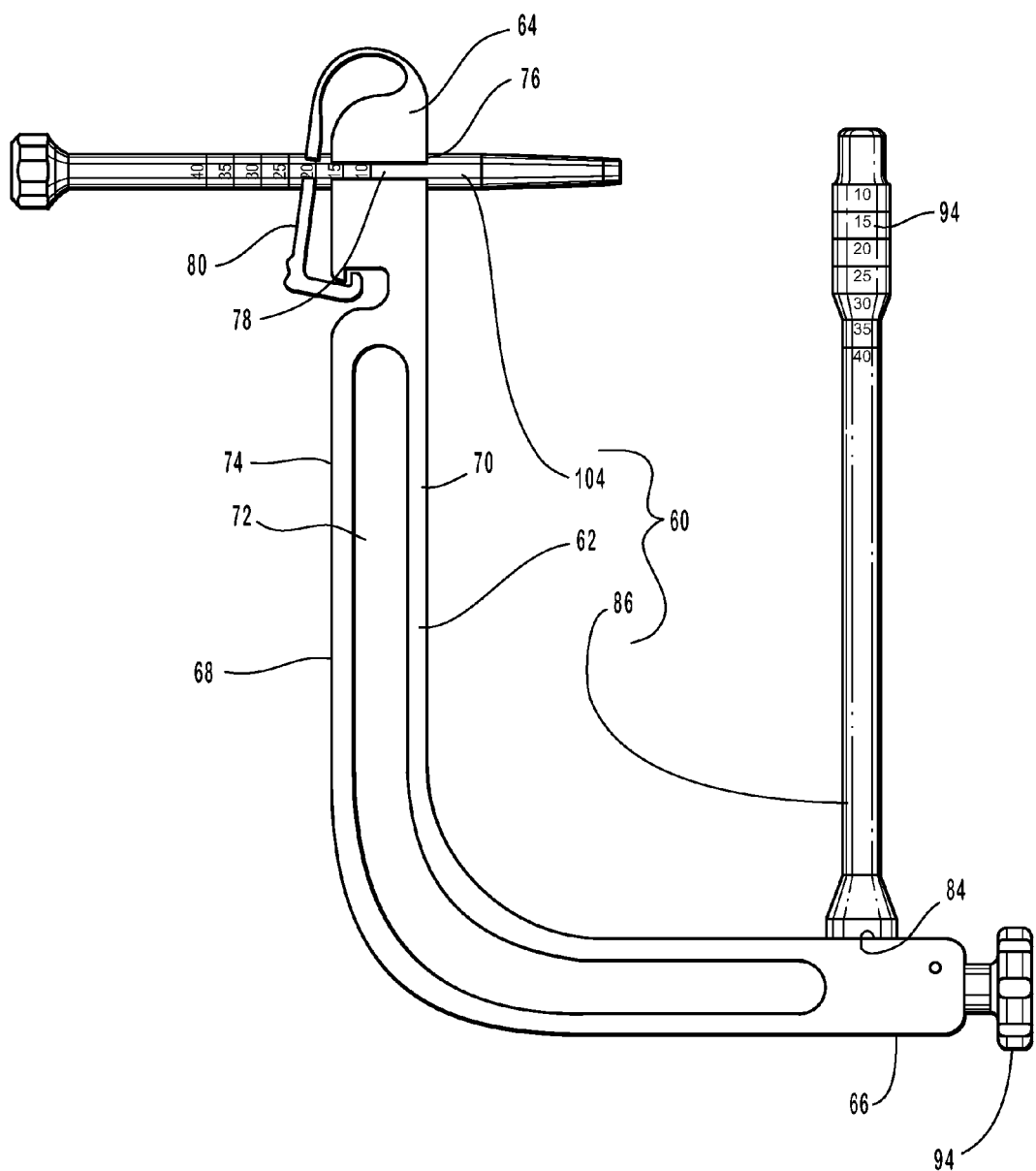
FIG. 4 is a top plan view of a complete drill guide.

Depicted in FIG. 3, once placement tunnel 20 is formed, reamer 36 is retracted and removed. Furthermore, drill pin 22 is raised upwardly within placement tunnel 20 such that forked tip 34 is disposed within access tunnel 53. With drill pin 22 removed from femoral tunnel 50, a transverse drill guide 60 is mounted to knee joint 18. Depicted in FIG. 4, drill guide 60 comprises a brace 62, a femoral index guide 86, and a cannulated guide bullet 104.

Brace 62 has a substantially L-shaped configuration that extends from a first end 64 to an opposing second end 66. Brace 62 includes an outside face 68, an inside face 70, and opposing side faces 72 and 74 extending therebetween. A passageway 84 transversely extends between faces 68 and 70 at second end 66 of brace 62. Mounted within passageway 84 is femoral index guide 86.

As depicted in FIGS. 5 and 6, femoral index guide 86 has a proximal end 88 and an opposing distal end 90. Proximal end 88 includes a stem 92 that is removeably received within passageway 84 of brace 62. A set screw 94 (FIG. 4) is used to secure stem 92 within passageway 84. A flange 93 outwardly projects distal of stem 92 and functions as a stop. An enlarged head 94 is formed at distal end 90 of index guide 86. Head 94 has a diameter substantially equal to the diameter of femoral tunnel 50 such that head 94 can be snuggly received therein. Head 94 terminates at a distal end face 96. A slot 98 is recessed within end face 96 and transversely extends across head 94.

Returning to FIG. 3, distal end 90 of femoral index guide 86 is passed through tibial tunnel 48 and received within femoral tunnel 50 such that slot 98 is laterally aligned within femoral head 12. Markings 100 are longitudinally spaced along the exterior of femoral index guide 86 so as to ensure that guide 86 is inserted to the proper depth.

As also shown in FIG. 3, a locking clip 80 is mounted at first end 64 of brace 62 so as to resiliently bias away from brace 62. A passageway 76 transversely extends through locking clip 80 and between outside face 68 and inside face 70 of first end 64 of brace 62. An access slot 78 communicates with passageway 76 along side face 72.

Figure 7:
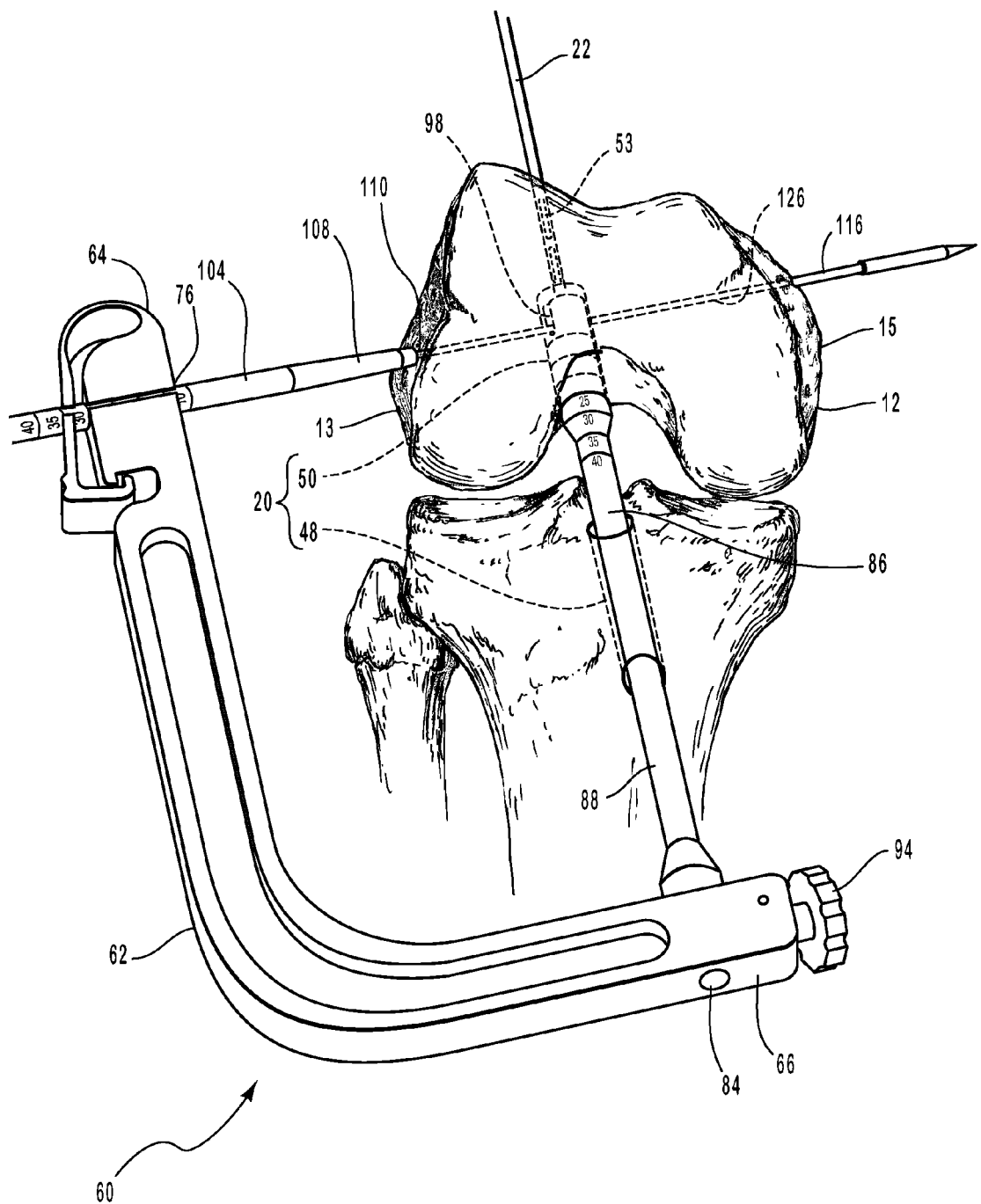
FIG. 7 is a front perspective view of a drill pin being laterally passed through a femoral head by use of the drill guide shown in FIG. 4.

Turning to FIG. 7, cannulated guided bullet 104 is received within passageway 76 of brace 62. As shown in FIG. 8, guide bullet 104 has a proximal end 106, an opposing distal end 108, and a passageway 110 centrally extending therebetween. Guide bullet 104 is advanced within passageway 76 so that distal end 108 biases against the lateral side 13 of femoral head 12. Clamp 80 flexes outward so as to secure guide bullet 104 in the desired location by frictional engagement. In this position, passageway 110 of guided bullet 104 is aligned with slot 98 of femoral index guide 86.

Returning to FIG. 7, once guide bullet 104 is appropriately positioned, a drill pin 116 is passed through passageway 110 of guide bullet 104 and then drilled through femoral head 12 from lateral side 13 to medial side 15 so as to pass through slot 98 of femoral index guide 86. In so doing, drill pin 116 forms a lateral guide tunnel 126 that extends laterally through femoral head 12 and intersects with femoral tunnel 50. As depicted in FIG. 9, drill pin 116 has a proximal end 118 and an opposing distal end 120. Proximal end 118 terminates at a threaded post 122 while distal end 120 terminates at a sharpened drill tip 124.

Figure 10:
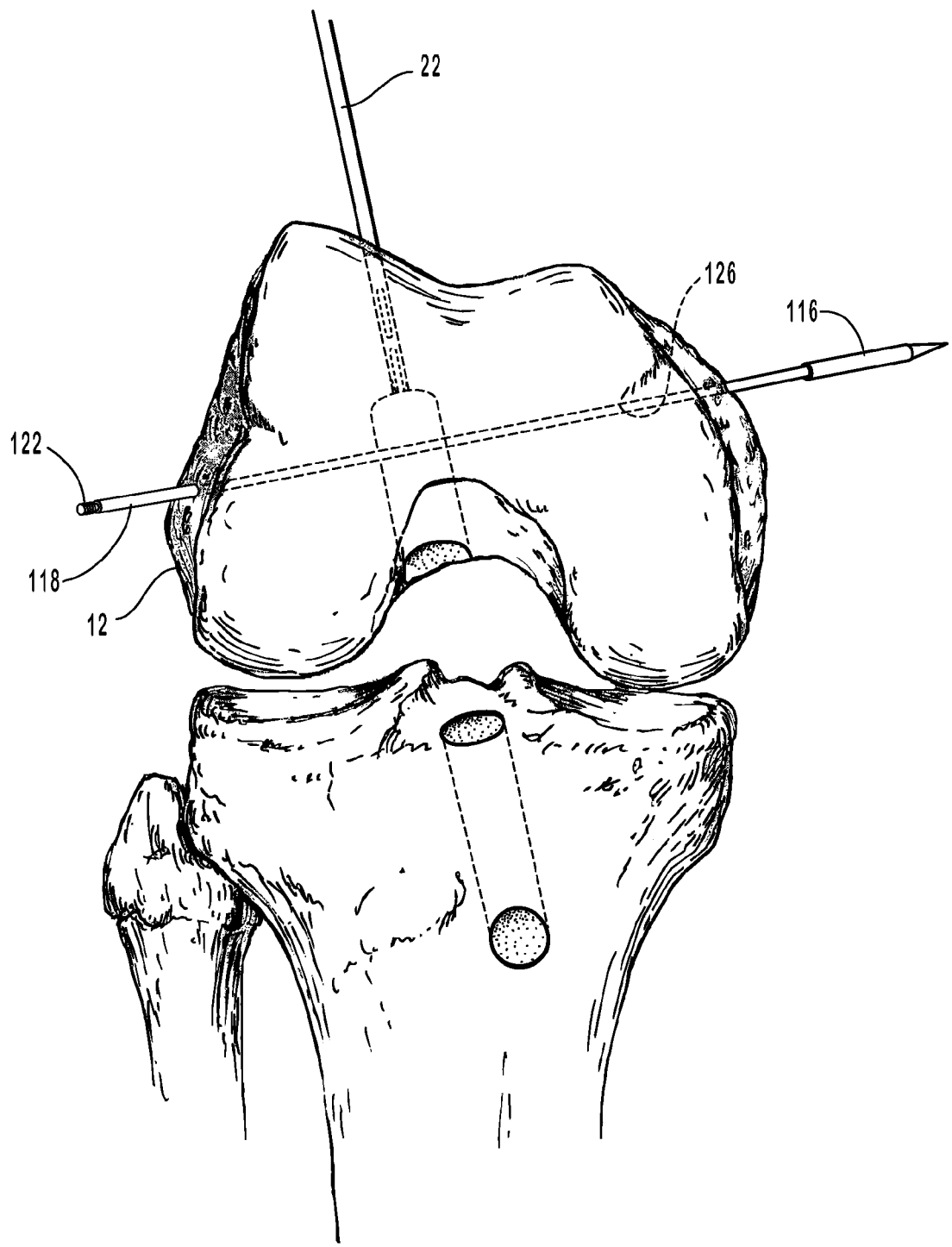
FIG. 10 is a front perspective view of the drill pin shown in FIG. 9 laterally extending through the femoral head with the drill guide removed.

Turning to FIG. 10, once drill pin 116 is passed through femoral head 12, transverse drill guide 60 is removed leaving drill pin 116 within femoral head 12. Drill guide 60 is removed by first pulling guide bullet 104 proximally off of drill pin 116 and out of passageway 76. Brace 62 is then rotated so that proximal end 118 of drill pin 116 slides out of passageway 76 through slot 78. Alternatively, drill pin 116 can be advanced distally until it exits passageway 76. Finally, femoral index guide 86 is retracted and removed from placement tunnel 20.

Figure 11:
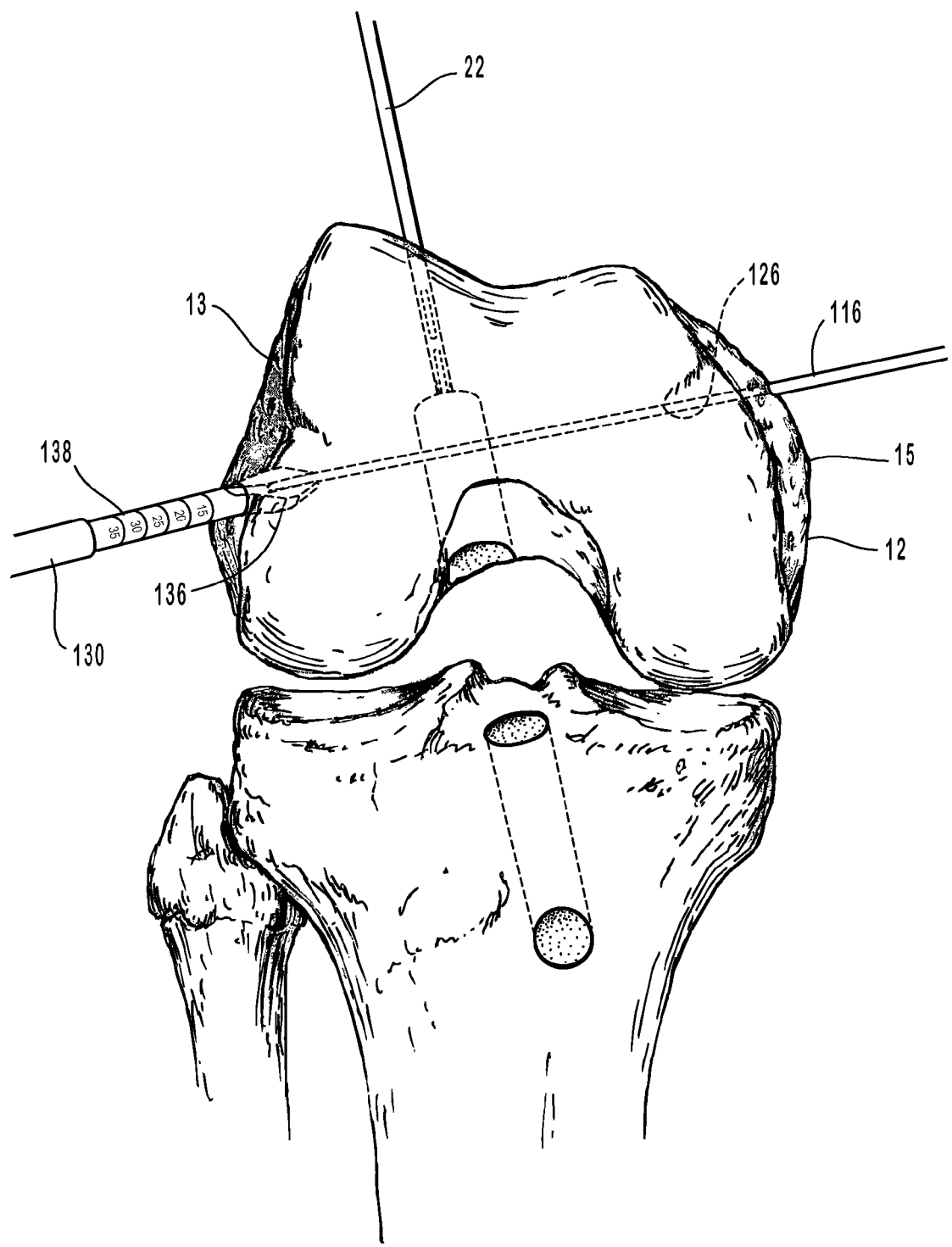
FIG. 11 is a front perspective view of a reamer being passed over the drill pin of FIG. 10 so as to form a counter bore in the femoral head.
Figure 12:
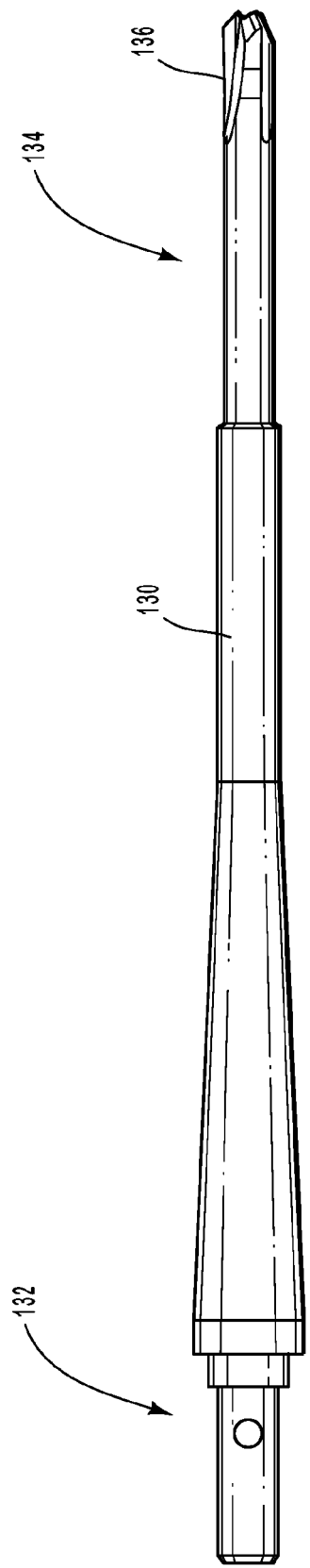
FIG. 12 is an elevated side view of the reamer shown in FIG. 11.
Figure 13:
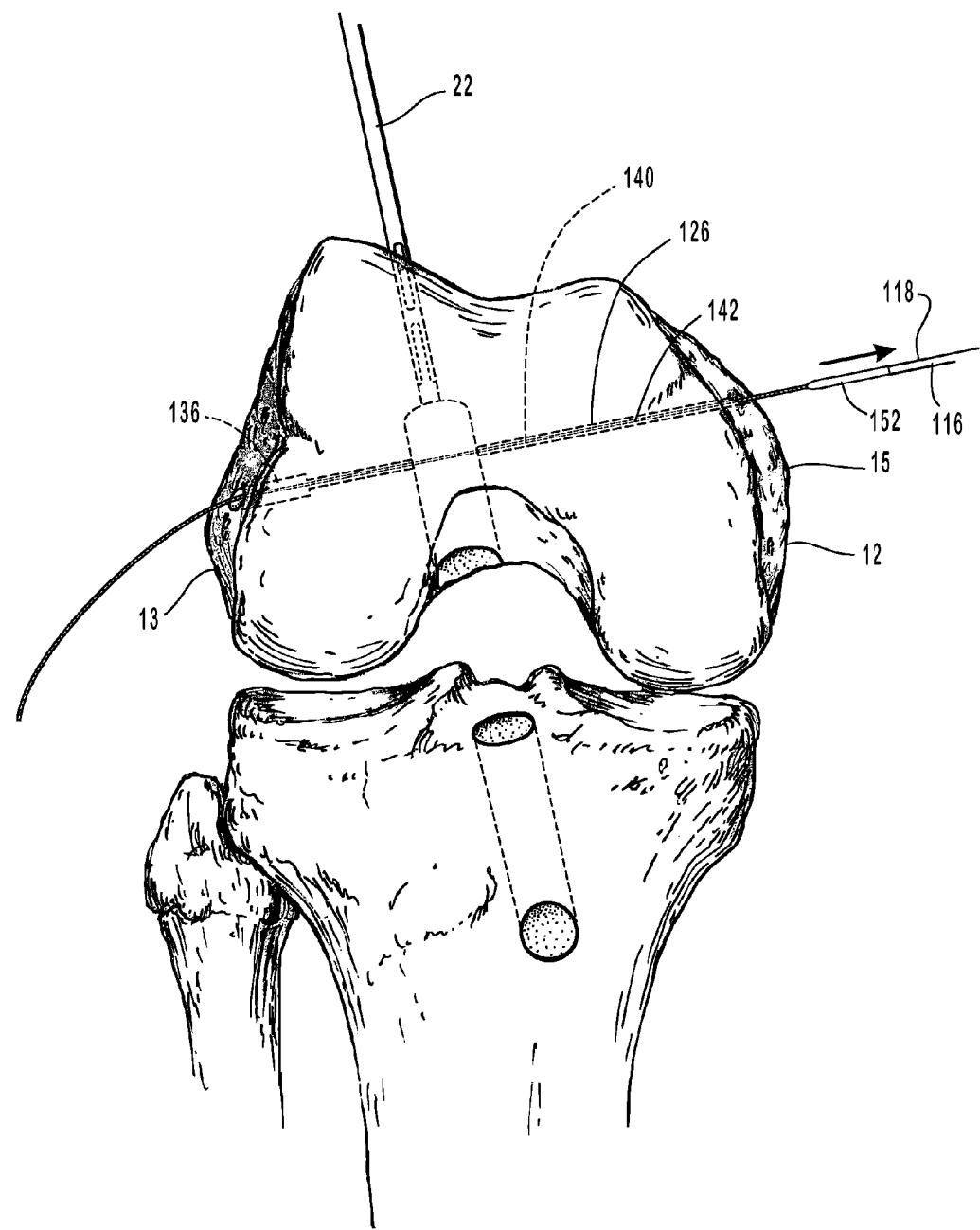
FIG. 13 is a front perspective view of a guide wire being passed through a lateral guide tunnel in the femoral head.

Next, as depicted in FIG. 11, a cannulated reamer 130, is next advanced over proximal end 118 of drill pin 116. As depicted in FIG. 12, reamer 130 has a proximal end 132 and an opposing distal end 134. Distal end 134 terminates at a fluted cutting tip 134 having a diameter lager than the diameter of lateral guide tunnel 126. Markings 138 are spaced longitudinally along the exterior surface of reamer 130 to ensure placement of reamer 130 to the proper depth. As depicted in FIGS. 11 and 13, using drill pin 116 as a guide, reamer 130 is advanced over drill pin 116 and drilled partially into lateral side 13 of femoral head 12 so as to form an enlarged counter bore 136.

Figure 14:
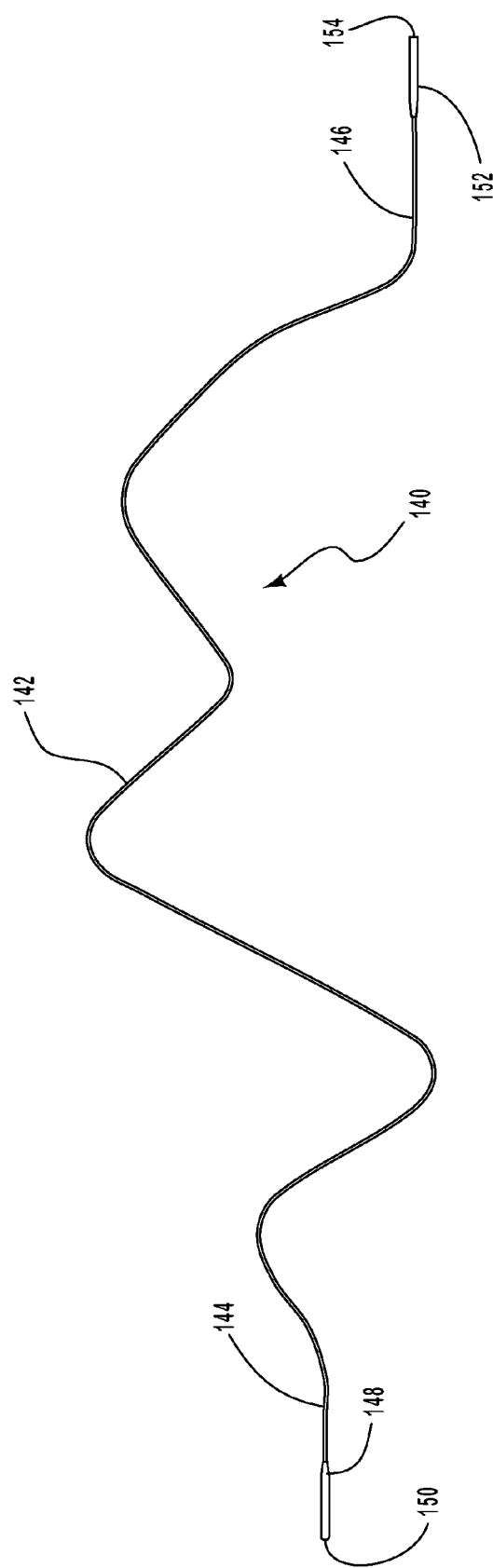
FIG. 14 is a partial cross section elevated side view of the guide wire shown in FIG. 13.

With proximal end 118 of drill pin 116 still projecting from lateral side 13 of femoral head 12 (FIG. 10), a guide wire 140 is removeably attached thereto. As depicted in FIG. 14, guide wire 140 comprises a flexible cable 142 having a proximal end 144 and an opposing distal end 146. Rotateably mounted on proximal end 144 of cable 142 is a proximal attachment sleeve 148. Attachment sleeve 148 bounds a threaded female socket 150 at the end thereof Similarly, a distal attachment sleeve 152 is rotateably mounted on distal end 146 of cable 142. Attachment sleeve 152 bounds a threaded female socket 154.

Guide wire 140 is secured to drill pin 116 by threading distal attachment sleeve 152 of guide wire 140 onto threaded post 122 (FIG. 9) of drill pin 116. Once guide wire 140 is coupled with drill pin 116, drill pin 116 is pulled through medial side 15 of femoral head 12 such that cable 142 is pulled within lateral guide tunnel 126, as shown in FIG. 13.

Figure 15:
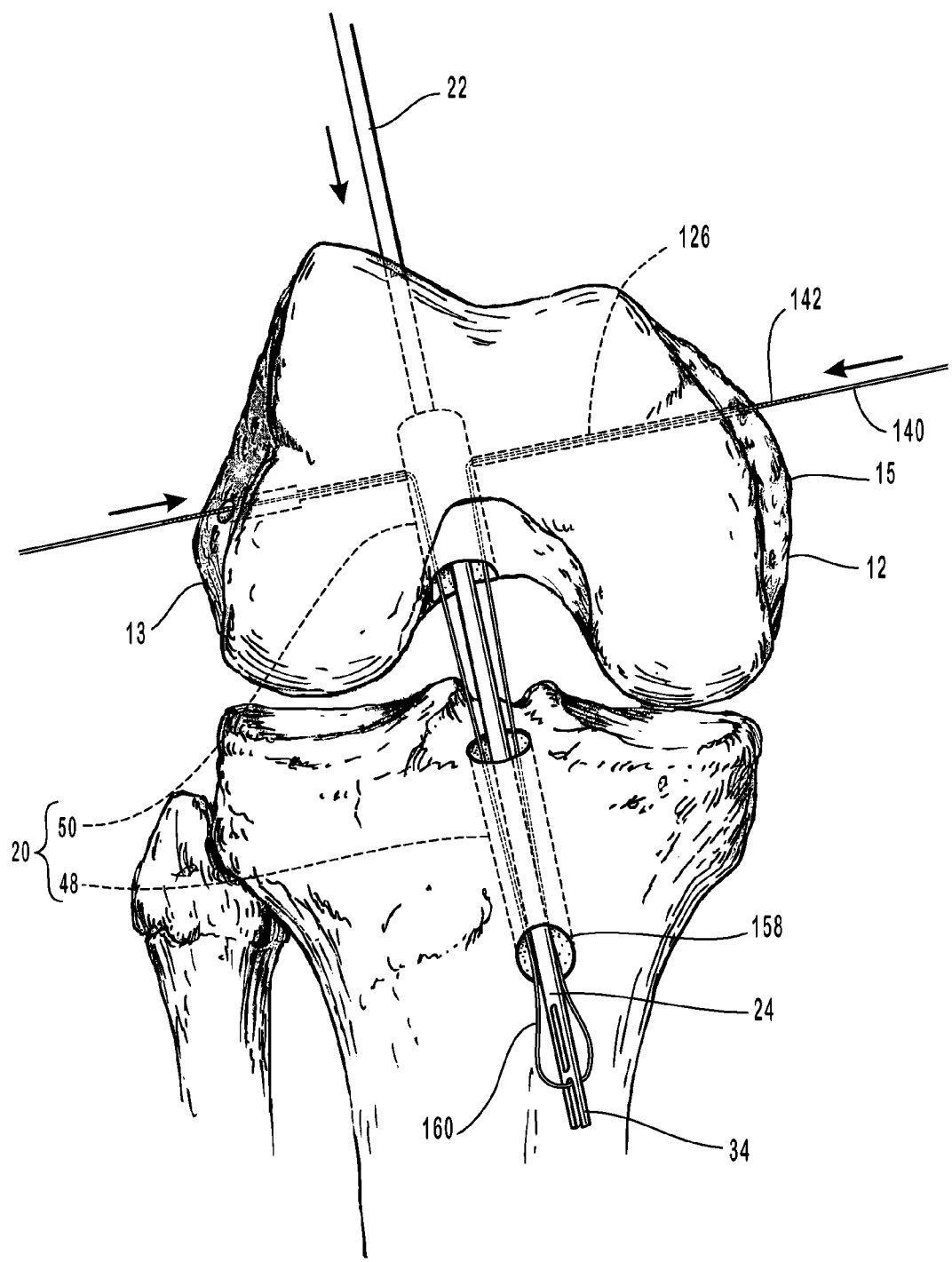
FIG. 15 is a front perspective view of the drill pin of FIG. 1 downwardly pushing the guide wire through the placement tunnel.

Next, as depicted in FIG. 15, drill pin 22 is advanced distally down through placement tunnel 20 so that proximal end 24 of drill pin 22 projects out through an anterior tibial opening 158 of tibial tunnel 48. As drill pin 22 is advanced through placement tunnel 20, cable 142 is captured between the prongs of forked tip 34. As a result, cable 142 is moved distally within placement tunnel 20 so that a loop 160 of cable 142 outwardly projects through anterior tibial opening 158.

Figure 16:
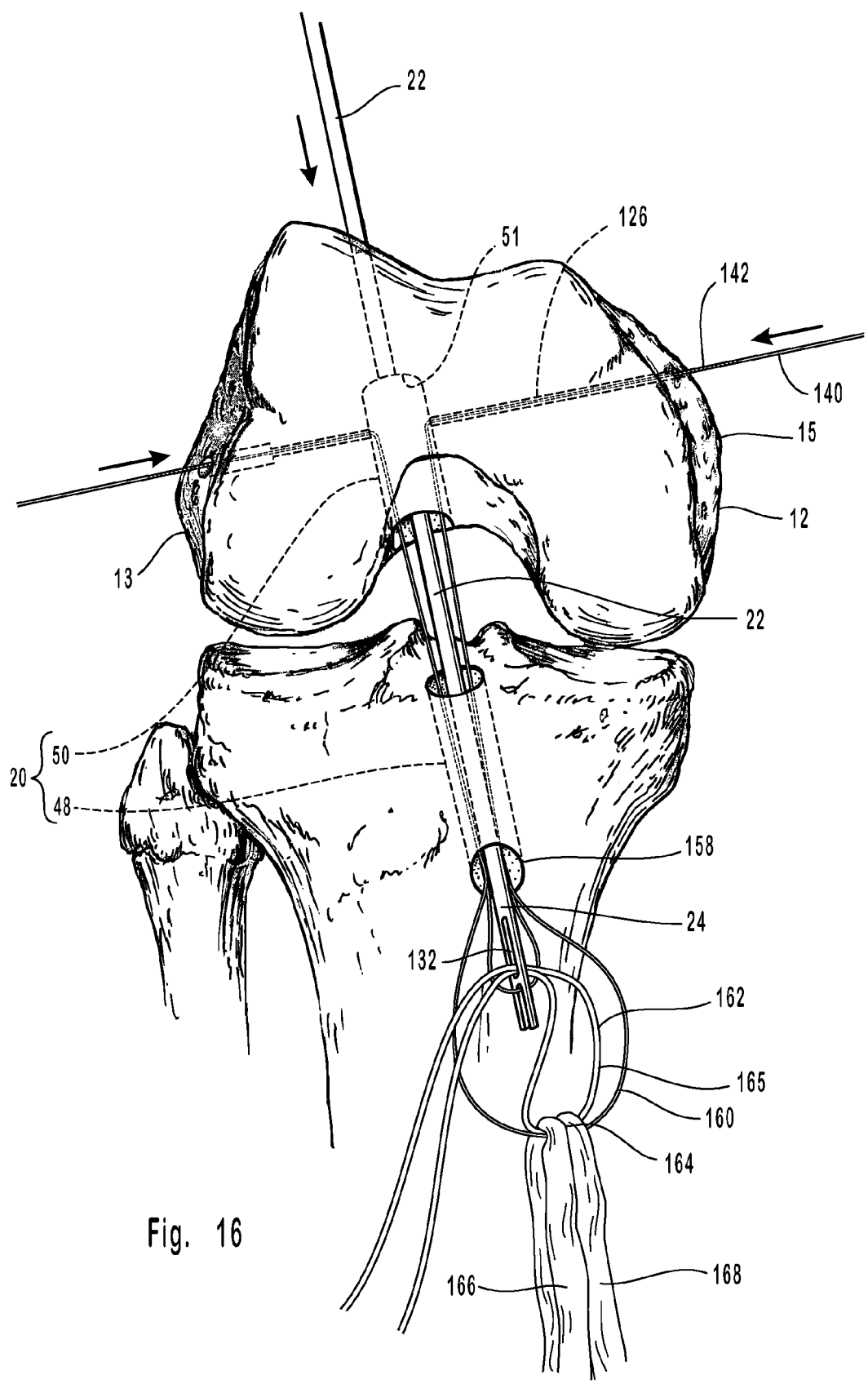
FIG. 16 is a front perspective view of a line securing a graft to the drill pin shown in FIG. 15, the graft being looped over the guide wire.

In this position, as shown in FIG. 16, a line 162 is used to secure a graft 164 to proximal end 24 of drill pin 22. Line 162 typically comprises a suture but can also comprise wire, cable, cord, filament, or any other type of line. In the embodiment depicted, as perhaps best seen in FIG. 16, graft 164 comprises two discrete strands 166 and 168. The strands are typically comprised of autograft, allograft, zenograft, synthetic graft or combinations thereof Each strand has a first end 170 and an opposing second end 172. A suture 173 and 174 is secured to fist end 170 of strands 166 and 168, respectively. Sutures are also typically secured to second end 170 of strands 166 and 168 and are used for manipulation of the strands and for ultimately securing the strands to the tibia. In alternative embodiments, the sutures are not required. Furthermore, graft 164 can comprise one or three or more strands. The strands of the graft can be left discrete or can be secured together.

Returning to FIG. 16, in one embodiment graft 164 is secured to drill pin 22 by forming a central portion of line 162 into a loop 165 and passing loop 165 through aperture 132 on drill pin 22. One end of graft 164 is then passed through loop 166 so that a central portion 175 of graft 164 is looped through and over loop 165. Graft 164 is also manipulated so that central portion 175 of graft 164 is looped over loop 160 of cable 142.

Figure 17:
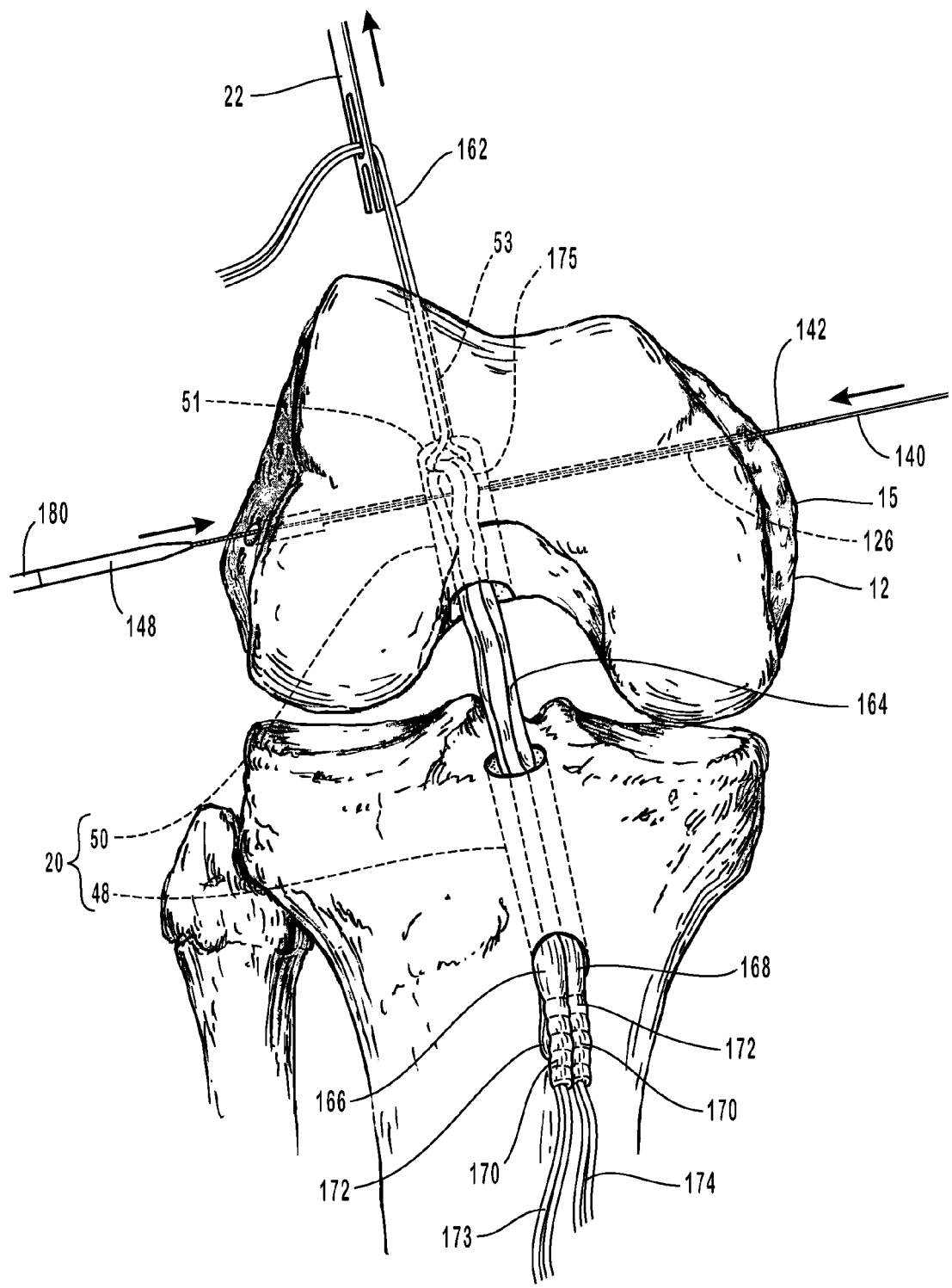
FIG. 17 is a front perspective view of the graft being pulled up into the placement channel by the drill pin.

Once in the above position, drill pin 22 is pulled proximally up through placement tunnel 22 and then out through access tunnel 53 as shown in FIG. 17. In so doing, the free ends of line 162 freely project out of access tunnel 53. The exposed ends of line 162 can concurrently pulled manually to ensure that graft 164 is pulled up against shoulder 51 of femoral tunnel 50. Line 162 can then be removed at any point in the procedure by simply pulling on one end of line 162.

It is noted that in the embodiment depicted, access tunnel 53 is large enough to allow drill pin 22 having line 162 passing therethrough to pass through access tunnel 53. However, access tunnel 53 is too small to allow graft 164 to pass therethrough. As such, shoulder forms a stop which functions to appropriately position graft 164 within placement tunnel 20.

Cable 142 is typically drawn up through placement tunnel 20 concurrently with drill pin 22 by pulling outward on one or both opposing ends of cable 142. It is noted, however, that the force used to pull graft 164 up into placement tunnel 20 is applied substantially, if not exclusively, by line 53. In alternative embodiments, however, it is appreciated that line 53 can be eliminated and graft 164 drawn up into placement tunnel 20 by simply pulling on opposing ends of cable 142.

Such use of cable 142, however, can result in cable 142 wearing into the bone at the intersection of lateral guide tunnel 126 and femoral tunnel 50. Furthermore, the angle of pulling can produce high-stresses on cable 142. The use of line 53 to pull graft 164 into placement tunnel 20 avoids these potential problems.

Figure 18:
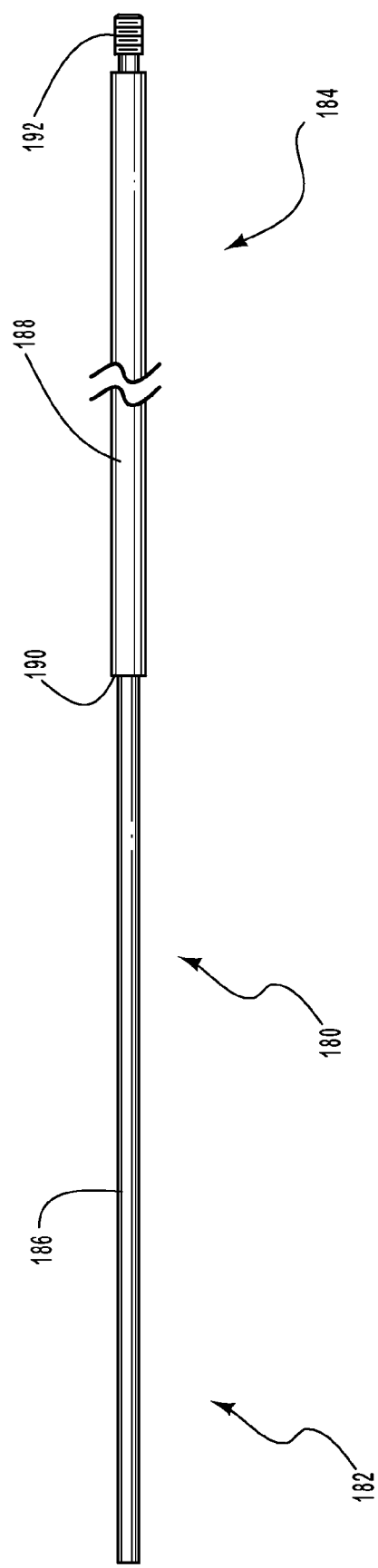
FIG. 18 is an elevated side view of a guide pin.

With the proximal end of guide wire 140 still projecting from lateral side 13 of femoral head 12, a stepped guide pin 180 is removeably mounted to proximal attachment sleeve 148. As depicted in FIG. 18, stepped guide pin 180 has a proximal end 182 and an opposing distal end 184. Guide pin 180 comprises a substantially cylindrical proximal shaft 186 and a substantially cylindrical distal shaft 188 which are axially aligned. Distal shaft 188 has an outer diameter larger than the outer diameter of proximal shaft 186 such that an annual shoulder 190 is formed therebetween. A threaded post 192 projects distally from distal shaft 188. Guide pin 180 connects with guide wire 140 by threading post 192 of guide pin 180 into socket 150 of proximal attachment sleeve 148.

Figure 19:
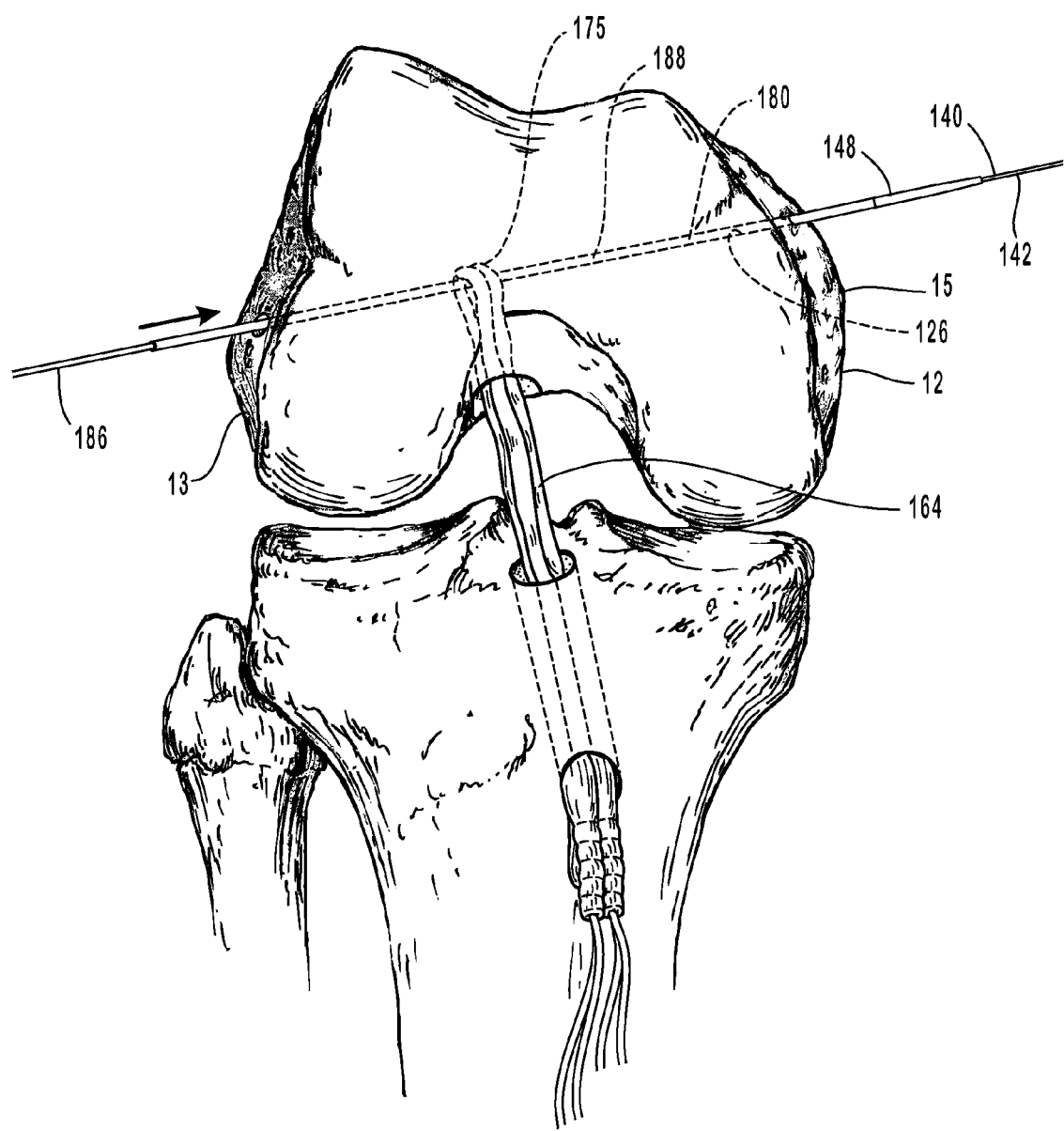
FIG. 19 is a front perspective view of the guide pin of FIG. 18 being attached to the guide wire and being pulled laterally through the femoral head so that the graft is looped thereover.

Next, as depicted in FIG. 19, guide wire 140 is pulled through medial side 15 of femoral head 12 so that guide pin 180 is received within lateral guide tunnel 126. Since guide pin 180 follows the same track as guide wire 142, guide pin 180 also passes through central looped portion 175 of graft 164.

Figure 20:
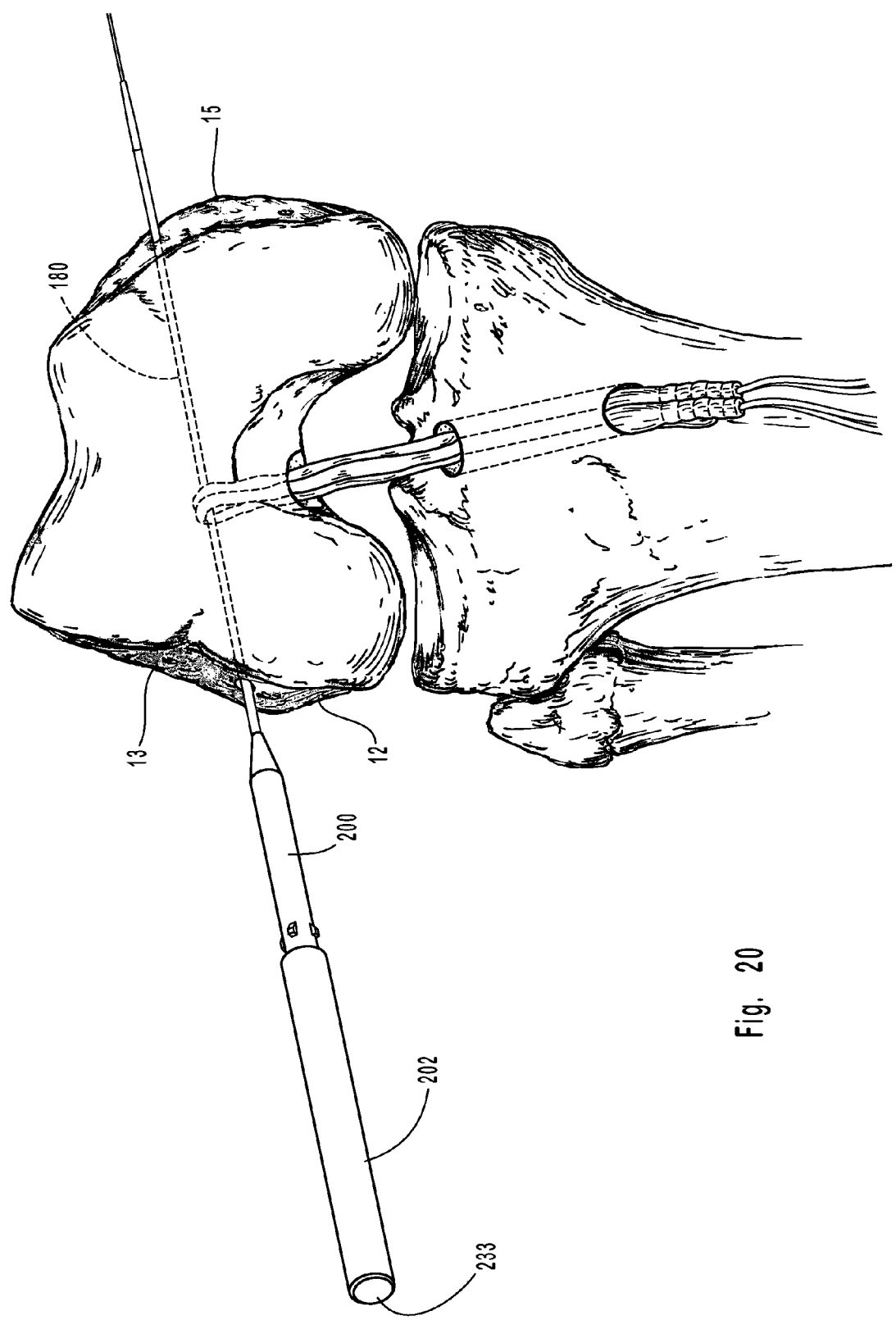
FIG. 20 is a perspective view of the guide pin shown in FIG. 19 having a cross pin and a tamp attached thereto.
Figure 21:
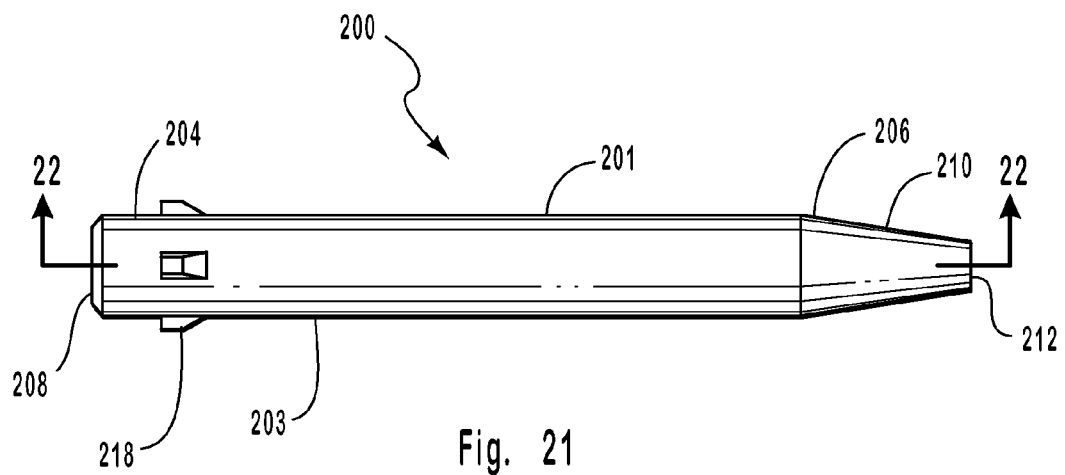
FIG. 21 is an elevated side view of the cross pin shown in FIG. 20.
Figure 22:
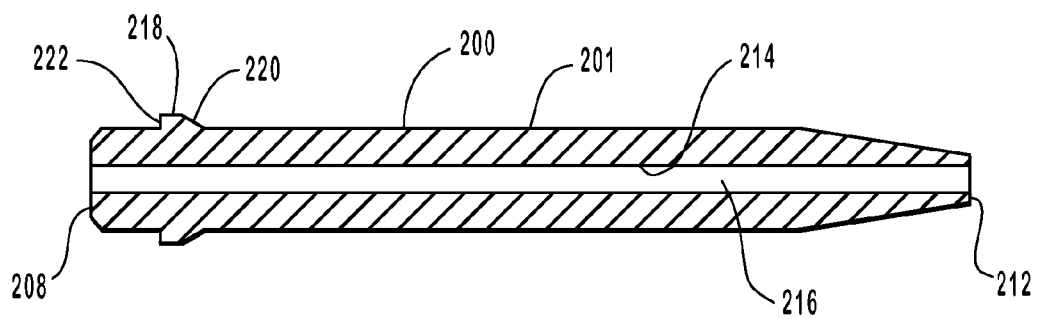
FIG. 22 is a cross section side view of the guide pin shown in FIG. 21.

Once guide pin 180 is inserted within lateral guide tunnel 126, a cross pin 200 and tamp 202 are mounted on proximal end 182 of guide pin 180 as shown in FIG. 20. Depicted in FIGS. 21 and 22, cross pin 200 has a substantially cylindrical body 201 having an exterior surface 203 that extends between a proximal end 204 and an opposing distal end 206. Proximal end 204 ends at a proximal end face 208. Distal end 206 has a frustoconical nose 210 that terminates at a distal end face 212. Body 201 has an interior surface 214 that bounds a passageway 216 extending between proximal end face 208 and distal end face 212. Radially outwardly projecting from exterior surface 203 at proximal end 204 are a plurality of radially spaced apart engagements ribs 218. Each engagement rib has a sloping distal face 220 and orthogonally projecting proximal face 222.

In alternative embodiments, it is appreciated that engagement ribs 218 can have a variety of alternative configurations. Furthermore, in contrasting to comprising a plurality of separate and discrete engagement ribs, engagement rib can comprise a continuous annular rib that encircles body 201.

Figure 23:
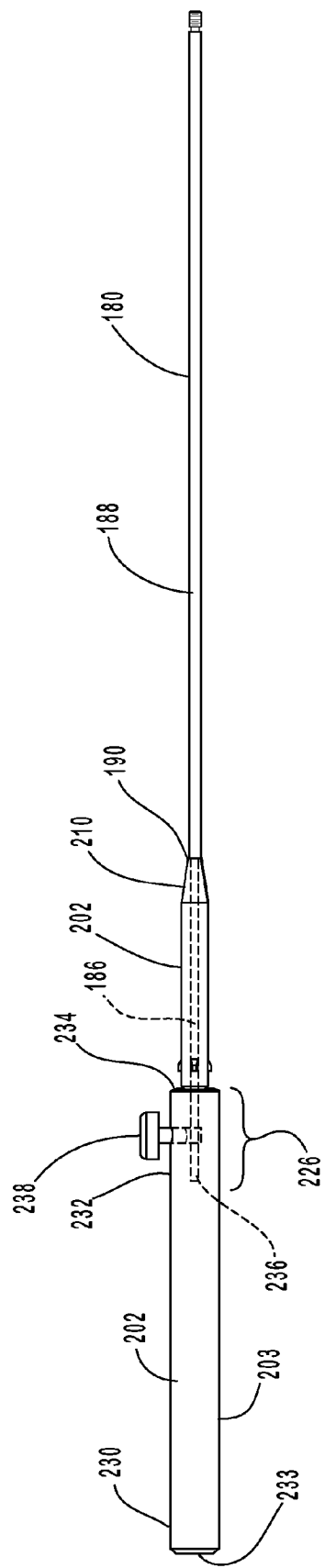
FIG. 23 is an elevated side view of the assembled guide pin, cross pin, and tamp.
Figure 24:
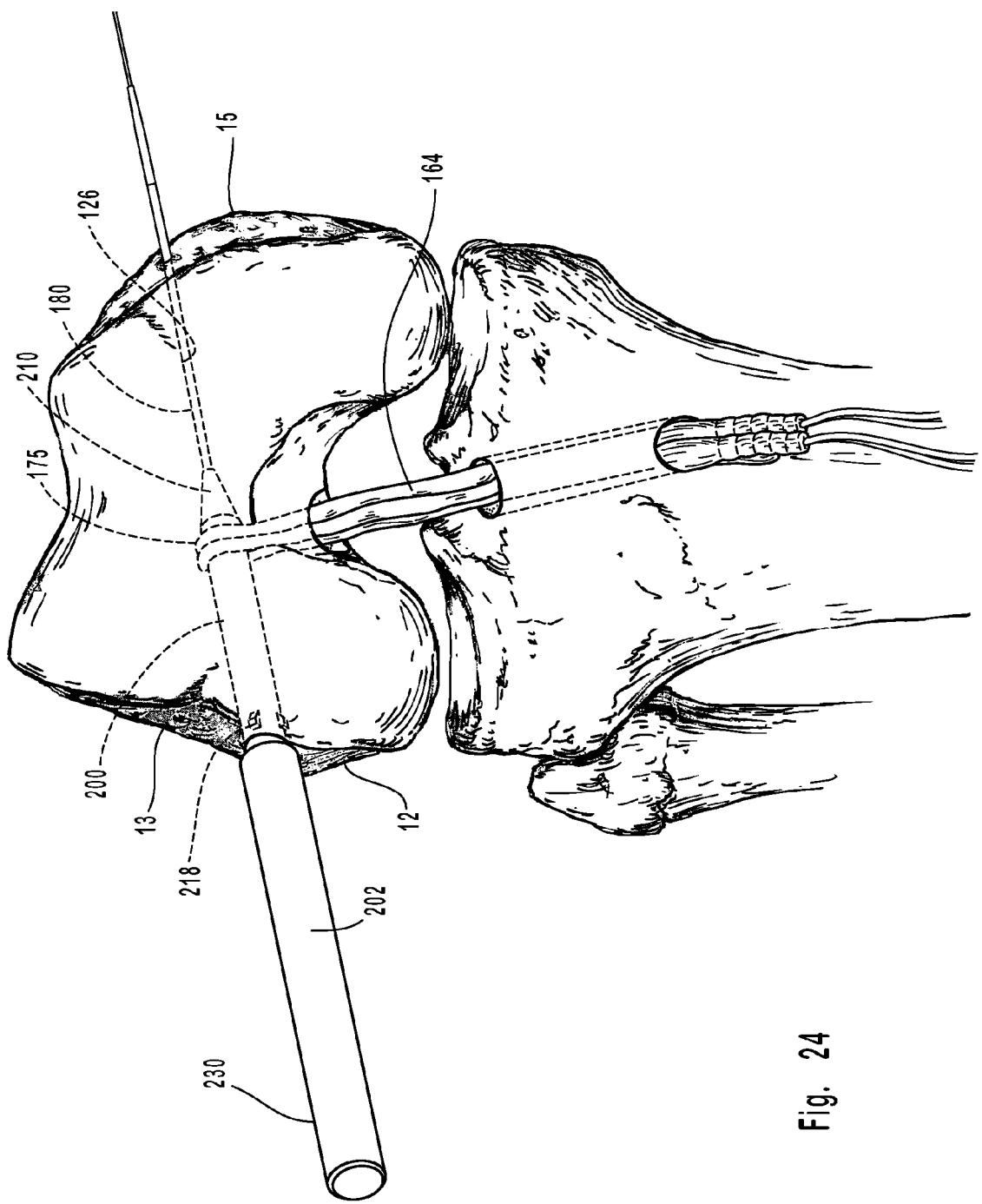
FIG. 24 is a front perspective view of the cross pin shown in FIG. 20 driven into the femoral head.

Cross pin 200 can be made in a variety of different ways using a variety of one or more different materials. By way of example and not by limitation, cross pin 200 can be made from medical grade biodegradable or non-biodegradable materials. Examples of biodegradable materials include biodegradable ceramics, biological materials, such as bone or collagen, and homopolymers and copolymers of lactide, glycolide, trimethylene carbonate, caprolactone, acetal copolymer, acetal homopolymer, silicone, ABS, polyetherarylketone, and p-dioxanone and blends or other combinations thereof and equivalents thereof The foregoing biodegradable materials are also examples of non-metallic materials that can be used. Examples of non-biodegradable materials include metals such as stainless steel, titanium, Nitinol, cobalt, alloys thereof, and equivalents thereof and polymeric materials such as non-biodegradable polyesters, polyamides, polyolefins, polyurethanes, and polyacetals and equivalents thereof As depicted in FIG. 23, proximal shaft 186 of guide pin 180 is received within passageway 216 of cross pin 200. Cross pin 200 is advanced over the proximal shaft 186 until cross pin 200 biases against shoulder 190 of guide pin 180. As will be discussed below in greater detail, cross pin 200 is ultimately driven into femoral head 12 such that cross pin 200 passes through central looped portion 175 of graft 164. To prevent damage to graft 164 as cross pin 200 is driven into femoral head 12, it is desirable to have a smooth transition between distal shaft 188 of guide pin 180 and frustoconical nose 210 of cross pin 200. Accordingly, although not required, in one embodiment distal end face 212 of cross pin 200 has an outer diameter that is substantially equal to or small than the outer diameter of distal shaft 188 of guide pin 180 at shoulder 190.

With cross pin 200 received on proximal shaft 186 of guide pin 180, it is noted that a segment 226 of proximal shaft 186 projects proximal of cross pin 200. Tamp 202 comprises a substantially cylindrical body 229 having a proximal end 230 and an opposing distal end 232. Body 229 is typically made of a metal, such as stainless steel, or other material that can be repeatedly impacted without fear of failure. Proximal end 230 of tamp 202 terminates at a proximal end face 205 while distal end 232 terminates at a distal end face 234. A bore 236 is axially formed within distal end face 234. Segment 226 of proximal shaft 186 is selectively received within bore 236. In turn, a set screw 238 is selectively threaded into distal end 232 of body 229 so as to engage against segment 226 of proximal shaft 186, thereby selectively securing tamp 202 to guide pin 180.

In the assembled configuration shown in FIG. 20, a mallet, hammer, or other tool used for impacting, is impacted against proximal end face 233 of tamp 202 so as to drive cross pin 200 into lateral guide tunnel 226. Guide pin 180 functions as a guide for cross pin 200 to ensure that it is driven into the appropriate position. As a result of using tamp 202, the impact delivered to cross pin 200 through tamp 202 is more uniformly distributed over proximal end face 208 of cross pin 200, thereby minimizing failure of cross pin 200 when cross pin 200 is made of a biodegradable material. That is, if a mallet was used to apply an impacting force directly to proximal end face 208 of cross pin 200, any impact off normal to end face 208 would produce a highly localized stress on cross pin 200. In contrast, by using tamp 202 even if the same off normal impact was applied to proximal end face 233 of tamp 202, the force transferred through tamp 202 to cross pin 200 would be more uniformly distributed over proximal end face 208, thereby minimizing localized stress and the potential for failure of cross pin 200. Another benefit of tamp 202 is that it protects portion 226 (FIG. 23) of guide pin 180 projecting proximal of cross pin 200.

It is noted that body 201 of cross pin 200 has an outer diameter that is larger than the inner diameter of lateral guide tunnel 126. As such, frusticonical nose 210 functions in part to radially outwardly compress the bone as cross pin 200 is driven into femoral head 12. Furthermore, barbs 218 bias into the bone at radially spaced apart positions so as to prevent migration and axial rotation of cross pin 200.

Cross pin 200 follows the same path as guide pin 180. Accordingly, as cross pin 200 is driven into femoral head 12, cross pin 200 passes through the looped central portion 175 of graft 164. Accordingly, when cross pin 200 is fully received within femoral head 12, graft 164 loops over and thus is centrally supported on cross pin 200. In one embodiment, cross pin 200 is driven into femoral head 12 until proximal end face 208 is substantially flush with lateral side 13. In alternative embodiments, cross pin 200 can be driven into femoral head 12 past lateral side 13. In this embodiment, at least distal end 232 of tamp 202 is formed having a diameter equal to or smaller than the diameter of the proximal end of cross pin 200. A shoulder or markings can be formed on tamp 202 to indicate the proper depth for cross pin 200.

In one embodiment, guide pin 180 is radiopaque. Thus, even when cross pin 200 is made of a biodegradable radiolucent material, x-rays and other forms of radiant energy can be used to ensure that cross pin 200 is appropriately positioned within femoral head 12. That is, by determining the position of guide pin 180, the position of cross pin 200 can also be determined.

Figure 25:
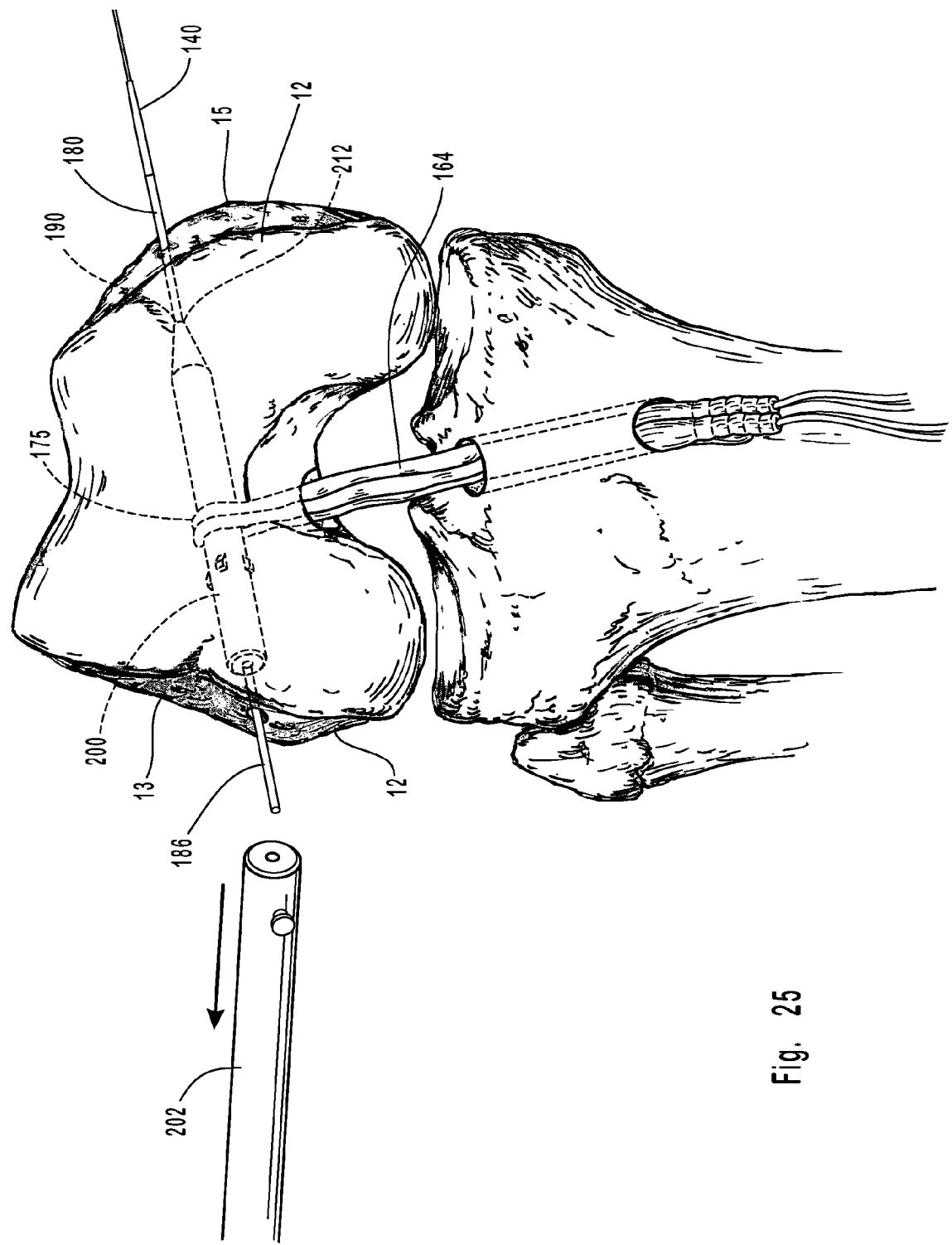
FIG. 25 is a front perspective view of the tamp shown in FIG. 24 being removed from the guide pin.

Furthermore, one of the unique benefits of one embodiment of the present invention is that cross pin 200 can be removed relatively easily from femoral head 12 should it be improperly placed. For example, to remove cross pin 200 from femoral head 12, tamp 202 is removed by sliding proximally off of guide pin 180 as shown in FIG. 25. Next, any number of conventional extraction tools can be secured to the exposed proximal shaft 186 of guide pin 180. It is appreciated that if tamp 202 is sufficiently secured to guide pin 180, the extraction tool can be directly connected to tamp 202. The extraction tool is then used to pull guide pin 180 through lateral side 13 of femoral head 12. As guide pin 180 is being removed, shoulder 190 of guide pin 180 biases against distal end face 212 of cross pin 200 such that cross pin 200 is pulled out of femoral head 12 concurrently with guide pin 180. It is also appreciated that either in conjunction with or independent of the use of the extraction tool, guide pin 180 can be impacted or otherwise pushed at distal end 184 to drive cross pin 200 out of femoral head 12.

The use of stepped guide pin 180 to remove cross pin 200 is unique to the present invention and provides a number of advantages. For example, in contrast to using stepped guide pin 180, the prior art cross pins use continuous annular threads on the proximal end thereof The threads enable the prior art cross pins to be removed by being unscrewed from the femoral head. There are, however, a number of drawbacks to using such threads.

For example, by having threads a feature must be formed on the cross pin that enables the cross pin to be engaged and rotated. In one prior art embodiment this is accomplished by forming a polygonal socket in the end of the cross pin. By forming the polygonal socket, however, the thickness of the wall of the cross pin is substantially thinned. As a result, such cross pins, particularly those made of brittle biodegradable material, are subject to increased failure during threaded insertion and removal. Although the size of the cross pin can be increased to increase the wall thickness, increasing the size of the cross pin has a number of inherent drawbacks.

An additional problem with threads formed on biodegradable cross pins is that it is often necessary to first tap complementary threads into the bone. Failure to tap complementary threads can result in failure of the biodegradable threads on the cross pin as the cross pin is initially threaded into the bone. Taping threads is a time consuming process that must be carefully done so that the cross pin is not inserted in an improper orientation.

As discussed above, cross pin 200 is unique in that it is free of threads. As such, cross pin 200 can be easily driven directly into femoral head 12 without tapping or threading. Furthermore, if required, cross pin 200 can be relatively easily removed by being pulled directly out of femoral head 12 without rotation.

Figure 26:
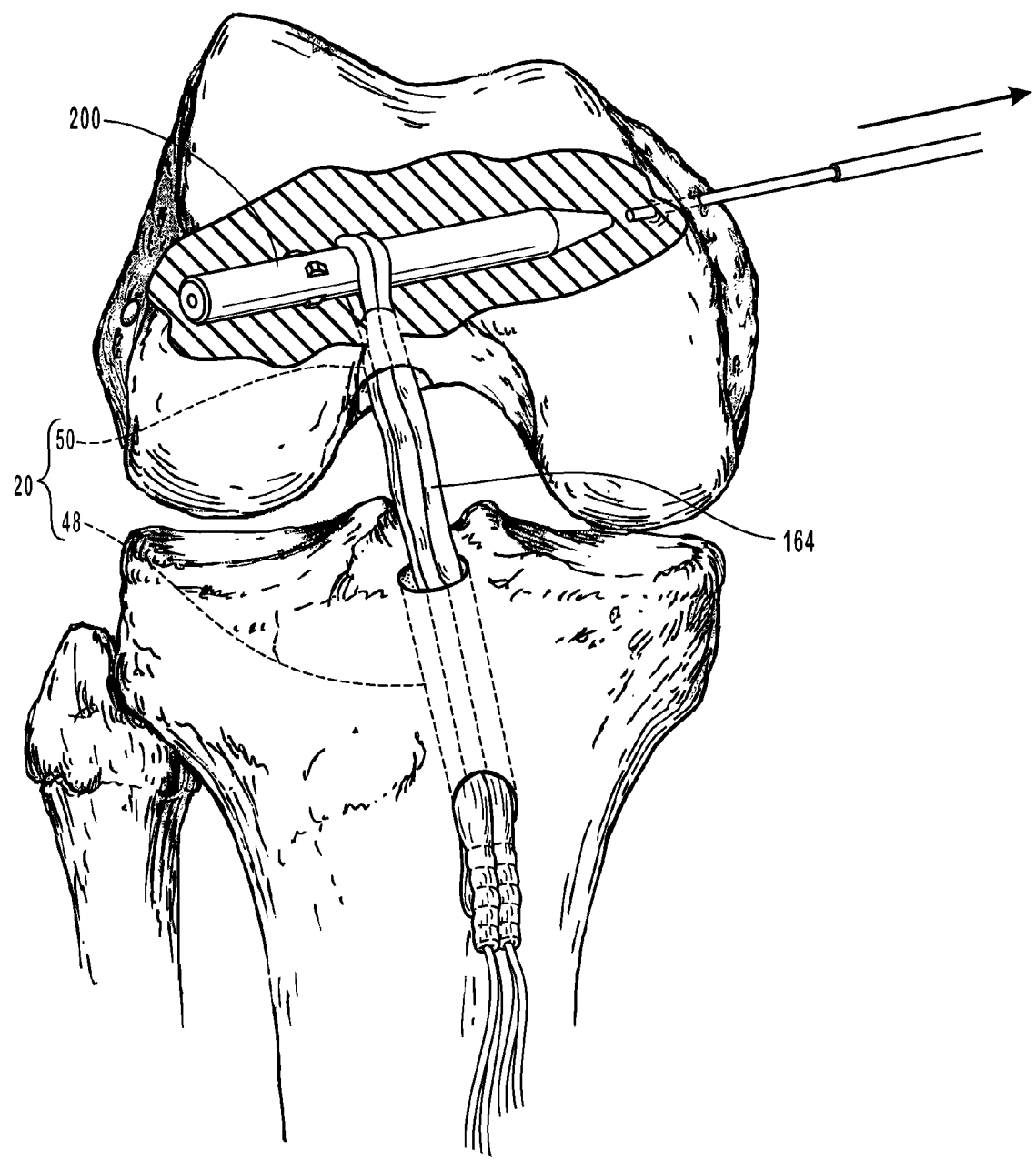
FIG. 26 is a front perspective view of the guide pin shown in FIG. 25 being removed from the cross pin.
Figure 27:
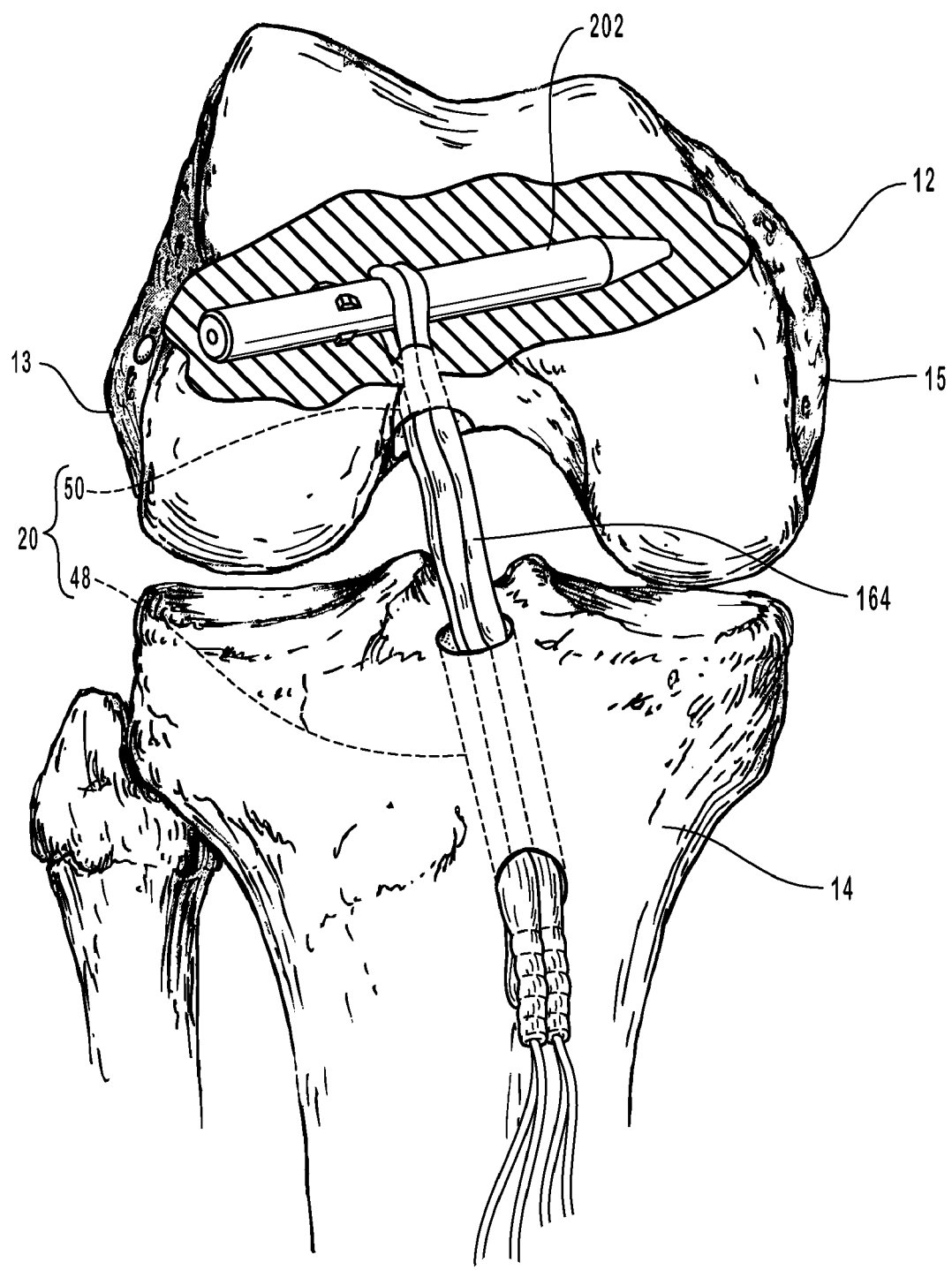
FIG. 27 is a front perspective view of the cross pin independently supporting the graft within the femoral head.

Once cross pin 200 is appropriately positioned, tamp 202 is removed by sliding proximally off of guide pin 180 as previously mentioned with regard to FIG. 25. As shown in FIG. 26, guide pin 180 is removed by sliding out through medial side 15 of femoral head 12. Cross pin is thus retained within femoral head 12, as shown in FIG. 27, so as to independently support graft 164 within placement tunnel 20. Conventional procedures can then be used to anchor or otherwise secure the free ends of graft 164 to tibia 14.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for securing a graft within a bone, the system comprising: a cannulated cross pin comprising an elongated cannulated body having an interior surface bounding a passageway extending between a proximal end and an opposing distal end of the cross pin so that the passageway extends completely through the cross pin, the distal end of the cross pin being frustoconically tapered and terminating at a distal end face, a plurality of radially spaced apart ribs outwardly projecting from the proximal end of the body, wherein the cross pin having a central longitudinal axis and with respect to the full length of the cross pin extending between the proximal end and the distal end, the cross pin having a maximum diameter that is measured normal to the central longitudinal axis of the cross pin; and a guide pin having an exterior surface extending between a proximal end and an opposing distal end, the exterior surface comprising an outwardly projecting shoulder located between the proximal end and the distal end, the guide pin being removably received within the passageway of the cross pin such that the distal end face of the cross pin biases against the shoulder so as to prevent the shoulder from passing through the passageway, and a proximal portion of the guide pin passes completely through the passageway of the cross pin and freely projects beyond the proximal end of the cross pin, wherein the guide pin having a central longitudinal axis and with respect to the full length of the guide pin extending between the proximal end and the distal end, the guide pin having a maximum diameter that is measured normal to the central longitudinal axis of the guide pin, the maximum diameter of the cross pin being greater than the maximum diameter of the guide pin.

2. A system as recited in claim 1, wherein the distal end face of the cross pin has a maximum outer diameter that is substantially equal to or smaller than a maximum outer diameter of the shoulder of the guide pin.

3. A system as recited in claim 1, wherein the guide pin comprises:
    an elongated cylindrical distal shaft having an exterior surface;
    an elongated cylindrical proximal shaft having an exterior surface, the proximal shaft having a maximum outer diameter smaller than a maximum outer diameter of the distal shaft; and
    the shoulder encircling and radially outwardly projecting from the exterior surface of the proximal shaft to the exterior surface of the distal shaft.

4. A system as recited in claim 3, wherein the proximal shaft is a solid shaft having no openings extending therethrough.

5. A system as recited in claim 3, wherein the shoulder is a flat annular ring that extends from the exterior surface of the proximal shaft to the exterior surface of the distal shaft.

6. A system as recited in claim 1, further comprising a tamp removably mounted on the proximal portion of the guide pin so as to bias against the proximal end of the guide pin.

7. A system as recited in claim 6, wherein the tamp has a distal end face with a bore formed thereon, the proximal end of the guide pin being received within the bore of the tamp so that the distal end face of the tamp biases against the proximal end of the cross pin.

8. A system as recited in claim 7, further comprising a set screw threaded into the tamp and engaging against the proximal end of the guide pin within the bore of the tamp.

9. A system as recited in claim 8, wherein the tamp has an exterior surface through which the set screw passes, the set screw having a first end engaging against the proximal end of the guide pin within the bore of the tamp and an opposing second end projecting a distance radially outward and away from the exterior surface of the tamp.

10. A system as recited in claim 8, further comprising an enlarged knob positioned at the second end of the set screw.

11. A system as recited in claim 1, further comprising a flexible guide wire mounted on the distal end of the guide pin.

12. A system as recited in claim 11, wherein the flexible guide wire is mounted to the guide pin by removable threaded engagement.

13. A system as recited in claim 11, wherein the flexible guide wire has a threaded first end and an opposing threaded second end.

14. A system as recited in claim 1, wherein the cross pin is comprised of a non-metallic material and the guide pin is comprised of a metal.

15. A system as recited in claim 1, further comprising a helical thread formed on the distal end of the guide pin.

16. A system as recited in claim 1, wherein the proximal end of the cross pin terminates at a proximal end face and a central longitudinal axis extends through the passageway of the cross pin and wherein with respect to the full length of the cross pin extending between the proximal end face and the distal end face, the cross pin has a maximum diameter that is measured normal to the central longitudinal axis, the maximum diameter being disposed within an imaginary plane that is normal to the central longitudinal axis and that intersects with at least one of the plurality of ribs.

17. A system as recited in claim 1, wherein the proximal end of the guide pin terminates at a proximal end face, the guide pin being sized so that the proximal end face can be passed through the entire length of the passageway of the cross pin.

18. A system as recited in claim 1, wherein all of the guide pin proximal of the shoulder is sized so as to be able to be disposed in or pass through the passageway of the cross pin.

19. A system as recited in claim 1, wherein the guide pin comprises a single unitary structure.

20. A system as recited in claim 1, wherein the diameter of the guide pin along the entire length of the guide pin proximal of the shoulder is less than or equal to the diameter of the passageway of the cross pin.

21. A system as recited in claim 1, wherein each of the plurality of ribs is linear and extends parallel to the passageway extending through the cross pin.

22. A system for securing a graft within a bone, the system comprising: a cannulated cross pin having an interior surface bounding a passageway extending between a proximal end and an opposing distal end of the cross pin so that the passageway extends completely through the cross pin, the distal end of the cross pin terminating at a distal end face, wherein the cross pin having a central longitudinal axis and with respect to the full length of the cross pin extending between the proximal end and the distal end, the cross pin having a maximum diameter that is measured normal to the central longitudinal axis of the cross pin; a guide pin having an exterior surface extending between a proximal end and an opposing distal end, the exterior surface comprising an outwardly projecting shoulder located between the proximal end and the distal end, the guide pin being removably received within the passageway of the cross pin such that the distal end face of the cross pin biases against the shoulder and a proximal portion of the guide pin passes completely through the passageway of the cross pin and freely projects beyond the proximal end of the cross pin, the diameter of the guide pin along the entire length of the guide pin proximal of the shoulder is less than or equal to the diameter of the passageway of the cross pin, wherein the guide pin having a central longitudinal axis and with respect to the full length of the guide pin extending between the proximal end and the distal end, the guide pin having a maximum diameter that is measured normal to the central longitudinal axis of the guide pin, the maximum diameter of the cross pin being greater than the maximum diameter of the guide pin; a tamp removably mounted on the proximal portion of the guide pin so as to bias against the proximal end of the guide pin, the tamp having a distal end face with a bore formed thereon, the proximal end of the guide pin being received within the bore of the tamp so that the distal end face of the tamp biases against the proximal end of the cross pin; and a set screw threaded into the tamp and engaging against the proximal end of the guide pin within the bore of the tamp.

23. A system as recited in claim 22, wherein the tamp has an exterior surface through which the set screw passes, the set screw having a first end engaging against the proximal end of the guide pin within the bore of the tamp and an opposing second end projecting a distance radially outward and away from the exterior surface of the tamp.

* * * * *